(12) United States Patent
Achilefu et al.

(10) Patent No.: US 7,850,946 B2
(45) Date of Patent: Dec. 14, 2010

(54) MACROCYCLIC CYANINE AND INDOCYANINE BIOCONJUGATES PROVIDE IMPROVED BIOMEDICAL APPLICATIONS

(75) Inventors: Samuel Achilefu, St. Louis, MO (US); Yunpeng Ye, Wildwood, MO (US)

(73) Assignee: Washington University in St. Louis, St. Louis, MO (US)

( * ) Notice: Subject to any disclaimer, the term of this patent is extended or adjusted under 35 U.S.C. 154(b) by 977 days.

(21) Appl. No.: 10/559,000

(22) PCT Filed: Jun. 1, 2004

(86) PCT No.: PCT/US2004/017142

§ 371 (c)(1),
(2), (4) Date: Nov. 30, 2005

(87) PCT Pub. No.: WO2005/000218

PCT Pub. Date: Jan. 6, 2005

(65) Prior Publication Data

US 2007/0098638 A1   May 3, 2007

Related U.S. Application Data

(60) Provisional application No. 60/474,453, filed on May 31, 2003.

(51) Int. Cl.
*A61K 51/00* (2006.01)
*A61M 36/14* (2006.01)

(52) U.S. Cl. .............. 424/1.69; 424/1.11; 424/1.49; 424/1.65; 424/1.73; 424/9.6

(58) Field of Classification Search ............. 424/1.11, 424/1.37, 1.65, 1.49, 1.69, 1.81, 9.1, 9.22, 424/9.3, 9.4, 9.5, 9.6, 9.7, 9.8; 540/1, 450; 544/1, 3, 63, 180, 224; 546/1, 152, 184, 546/249; 548/100, 146, 215, 255, 300.1, 548/400; 549/1, 200; 530/300, 330

See application file for complete search history.

(56) References Cited

U.S. PATENT DOCUMENTS 5,453,505 A   9/1995  Lee et al.

6,217,848 B1   4/2001  Achilefu et al.

FOREIGN PATENT DOCUMENTS

| WO | WO9617628 A1 | 6/1996 |
| WO | WO9822146 A2 | 5/1998 |
| WO | WO9848838 A1 | 11/1998 |
| WO | WO9848846 A1 | 11/1998 |

OTHER PUBLICATIONS

Bremer, C., et al.; "Imaging of differential protease expression in breast cancers for detection of aggressive tumor phenotypes", Radiology 222, pp. 814-818, 2002.
Brinkley M., "A Brief Survey of Methods for Preparing Protein Conjugates with Dyes, Haptens, and Cross-Linking Reagents", Perspectives in Bioconjugate Chemistry, (Ed. Claude Meares, ACS Publication, Washington D.C.), pp. 59-70, 1993.
Bugaj, J.E., et al.; "Novel fluorescent contrast agents for optical imaging of in vivo tumors based on a receptor-targeted dye peptide conjugate platform". Journal of Biomedical Optics, pp. 122-133, vol. 6, No. 2, Apr. 2001.
Dejong, M., et al. "Comparison of (111)In-labeled somatostatin analogues for tumor scintigraphy and radionuclide therapy" Cancer Research 58; pp. 437-441, 1998.
Jain, R.K., "Barriers to Drug Delivery in Solid Tumors", Scientific American, 271, pp. 58-65, 1994.
Lewis, J.S. et al., "Comparison of Four 64Cu-labeled Somatostatin Analogs in vitro and in a Tumor-bearing Rat Model: Evaluation of New Derivatives of PET Imaging and Targeted Radiotherapy" Journal of Medicinal Chemistry, 42, pp. 1341-1347, 1999.
Weissleder, R., "A clearer vision for in vivo imaging", Nature Biotechnology, 19, 316-317, 2001.
Becker et al., "Transferrin-mediated tumor delivery of contrast media for optical imaging and magnetic resonance imaging"; Proceedings of biomedical imaging; reporters, dyes, and instrumentation, Jan. 26-28, 1999, pp. 142-150.
Patonay et al., "Near-Infrared Fluorogenic Labels: New Approach to an Old Problem", Analytical Chemistry, vol. 63, No. 6, pp. 321A-327A.
International Search Report dated Dec. 27, 2004, 3 pages.

*Primary Examiner*—D L Jones

(57) ABSTRACT

The sensitivity and specificity of the optical modality can be enhanced by the use of highly absorbing compounds as contrast agents. Novel macrocyclic cyanine and indocyanine bioconjugates that absorb and emit light in the near infrared region of electromagnetic spectrum are disclosed. These compounds are especially useful for endoscopic, localized photoacoustic, and sonofluorescence imaging, detection and therapy of tumors and other abnormalities.

3 Claims, 14 Drawing Sheets

A

ICG

B

MACROCYCLIC CYANINE AND INDOCYANINE BIOCONJUGATES PROVIDE IMPROVED BIOMEDICAL APPLICATIONS

CROSS REFERENCE TO RELATED APPLICATIONS

This application claims the benefit of provisional application Ser. No. 60/474,453 filed May 31, 2003 and PCT application, International Application Number PCT/US04/17142, filed Jun. 1, 2004.

STATEMENT OF GOVERNMENT INTEREST

This invention was made with government support under grant number BES-01194889 (NSF). The federal government has certain rights in this invention.

BACKGROUND OF THE INVENTION

1. Field of the Invention

This invention relates generally to improved cyanine and indocyanine bioconjugates; and, particularly to improved site-specific delivery for optical tomographic, endoscopic, photoacoustic, sonofluorescent, laser assisted guided surgery, and therapeutic purposes.

2. Background of the Prior Art

Several dyes, including derivatives of fluorescein and carbocyanine, that emit light in the visible and near-infrared region of the electromagnetic spectrum have in the past and are currently being used for various biomedical applications due to their biocompatibility, high molar absorptivity, or high fluorescence quantum yields. This high sensitivity parallels that of nuclear medicine and permits visualization of organs and tissues without the negative effect of ionizing radiation. Most dyes lack specificity for particular organs or tissues and, hence, these dyes must be attached to bioactive carriers such as proteins, peptides, carbohydrates, and the like to deliver the dyes to specific regions in the body. Several studies on the use of near infrared dyes and dye-biomolecule conjugates have been published (Patonay et al., 1991; Slavik, 1994 Brinkley, 1993; Lee and Woo, U.S. Pat. No. 5,453,505; Hohenschuh, WO 98/48846; Turner et al., WO 98/22146; Licha et al., WO 96/17628; and Snow et al., WO 98/48838). Of particular interest is the targeting of tumor cells with antibodies or other large protein carriers as delivery vehicles (Becker, et al., 1999). Such an approach has been widely used in nuclear medical applications, and the major advantage is the retention of a carrier's tissue specificity since the molecular volume of the dye is substantially smaller than the carrier. However, this approach does have some serious limitations in that the diffusion of high molecular weight bioconjugates to tumor cells is highly unfavorable, and is further complicated by the net positive pressure in solid tumors (Jain, 1994). Furthermore, many dyes in general, and cyanine dyes, in particular, tend to form aggregates in aqueous media that lead to fluorescence quenching.

Therefore, to solve these problems, U.S. Pat. No. 6,217,848 disclosed dye-peptide conjugates, including several cyanine dyes with a variety of bis- and tetrakis (carboxylic acid) homologues. The small size of the compounds allowed more favorable delivery to tumor cells, as compared to larger molecular weight imaging agents.

A typical example of the cyanine compounds used to make these conjugates is indoacyanine green (ICG) which absorbs and emits light in the near infrared region (NIR) wavelengths. However, many drawbacks have been encountered in the use of these recently developed compounds. First, it is difficult to alter their spectral properties to coincide with a desired biological or chemical event, thereby limiting the scope of their functionality as imaging agents. For example, the fluorescence emission and fluorescence lifetime of ICG, in the tissue itself, do not significantly change in situ; and hence, the ICG derivatives cannot be used effectively as a reporter molecules to monitor the functional events such as enzyme activity, and gene expression, as they occur. To circumvent this problem, recent studies have used a "pro-drug" approach, where the fluorescence signal, from a pre-quenched carbocyanine compound, is detected in response to a diagnostic biological event, such as increased local acidity in solid tumors, or high expression of some proteases in metastatic tumors [Bremer C., et al,. "Imaging of differential protease expression in breast cancers for detection of aggressive tumor phenotypes", *Radiology* 222, 814-818 (2002); Weissleder R., "A clearer vision for in vivo imaging", *Nat. Biotechnol.* 19, 316-317 (2001)].

Unfortunately, this "pro-drug" approach relies on the stacking of dyes on a polymer backbone to achieve some level of decrease in fluorescence emission. In addition, the large size of the copolymer-probe conjugate used precludes rapid delivery of the probe to solid tumors. Moreover, the delivery method is nonspecific and the major photophysical feature of the dye that was affected was a reduction in the fluorescence emission of the polymeric material, rather than the tissue itself. Thus, availability of intramolecularly-quenched carbocyanine compounds, coupled with specific delivery to target tissue for functional imaging events such as enzyme activity and gene expression remain an unmet need.

Another problem with the recent carbocyanine dye-bioconjugates, is in vivo instability. That is, the bioactive carrier molecule, such as a peptide, is attached to the dye via its N-terminus, where the peptide is susceptible to degradation by exopeptidases via the C-terminus.

Also, the routine use of cyanine bioconjugate compounds in clinical settings as imaging agents is inhibited by the potential for hepatobilliary toxicity resulting from the rapid clearance of these dyes by the liver. This is associated with the tendency of carbocyanine compounds to form aggregates in solution, which could be taken up by Kupffer cells in the liver. Various attempts to obviate this problem have not been very successful. Typically, hydrophilic peptides, polyethyleneglycol or oligosaccharide conjugates have been used but these resulted in excessively long-circulating products that are eventually cleared by the liver.

It would be a welcomed advancement in the industry to overcome the aforesaid drawbacks of the prior art.

The publications and other materials used herein to support the background of the invention or provide additional details respecting the practice, are incorporated by reference, and for convenience are respectively listed in the appended List of Reference.

SUMMARY OF THE INVENTION

In one principal aspect of the present invention there is improved ease with which to alter the spectral properties of cyanine bioconjugates as a function of particular biological or chemical events.

In another principal aspect of the invention there is an improvement in the delivery of the bioconjugates to targeted tumors or other biomasses.

Also, an unexpected aspect of this invention is that the macrocyclic bioconjugates have improved stability, as far example, against degradation by exopeptidases, while retaining high receptor binding affinity of peptides, even though carboxyl, alcoholic or otherwise terminal substituents are not free.

Also, although not completely understood, it is believed that a further aspect of the invention may allow solvent-induced aggregation in solution to be disrupted, and allow a unique mechanism for the bioconjugates to more rapidly clear the liver.

These aspects of the invention and others which will become more apparent from the ensuing Summary, Detailed Description, Figures and Examples, are made possible by intramolecularly cross-linked carbocyanine, cyanine or indocyanine bioconjugates including cross-linked bioconjugates of fluorescein, porphyrin, squarine and their derivatives, useful as imaging agents, hereinafter referred to as macrocyclic bioconjugates having Formulas 1-18 below:

The present invention comprises novel macrocyclic bioconjugate imaging agents, among which are those defined as Formula 1:

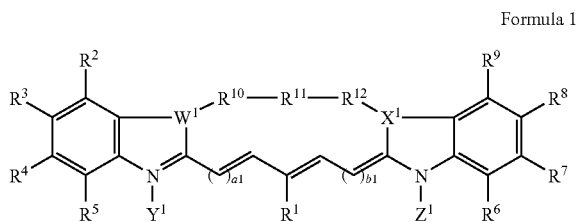

Formula 1 wherein a1 and b1 vary from 0 to 7; $W^1$ and $X^1$ are independently selected from the group consisting of $CR_a$, $NR_b$, P, $P(O)R_c$; $Y^1$ and $Z^1$ are independently selected from the group consisting of —H, —$CR_aR_b$, C1-C10 alkyl, C1-C10 aryl, C1-C10 alkoxyl, C1-20 polyalkoxyalkyl, C1-10 thioalkyl, C1-C10 carboxylic acid, C1-C10 aminoalkyl, C1-C10 hydroxyalkyl, C5-C20 polyhydroxyaryl, —$(CH_2)_a$—$NR_aR_b$, —$CH_2(CH_2$—O—$CH_2)_b$—$CH_2$—$OR_e$, —$(CH_2)_a$—$CO_2R_e$, —$CH_2$—$(CH_2$—O—$CH_2)_b$—$CH_2$—$CO_2R_e$, —$CH_2$—$(CH_2$—O—$CH_2)_b$—$CH_2$—$NR_aR_b$, —$(CH_2)_a$—$N(R_b)$—$(CH_2)_c$—$CO_2R_e$, —$(CH_2)_a$—$N(R_b)$—$CH_2$—$(CH_2$—O—$CH_2)_b$—$CH_2$—$CO_2R_e$, —$(CH_2)_a$—$CONR_b$-Bm, —$CH_2$—$(CH_2$—O—$CH_2)_b$—$CH_2$—$CONR_b$-Bm, —$(CH_2)_a$—$NR_bCO$-Bm, —$CH_2$—$(CH_2$—O—$CH_2)_b$—$CH_2NR_bCO$-Bm, —$(CH_2)_a$—$NR_bCO$-Bm, —$CH_2$—$(CH_2$—O—$CH_2)_b$—$CH_2NR_bCO$-Bm, —$(CH_2)_a$—$N(R_b)$—$(CH_2)_c$—$CONR_b$-Bm, —$(CH_2)_a$—$N(R_b)$—$CH_2$—$(CH_2$—O—$CH_2)_b$—$CH_2$—$CONR_b$-Bm, —$(CH_2)_a$—$SO_3R_e$, —$(CH_2)_b$S(O)$R_e$, —$(CH_2)_aSR_e$, —$(CH_2)_aOSO_3R_e$, —$(CH_2)_aNR_bSO_3R_e$, —$(CH_2)_aCO_2(CH_2)_bSO_3$—$(CH_2)_aSO_3R_e$, —$(CH_2)_aOCO(CH_2)_cSO_3R_e$, —$(CH_2)_a$ $CONR_b(CH_2)_cSO_3R_e$, —$(CH_2)_aNR_bCO(CH_2)_cSO_3R_e$, —$(CH_2)_aNR_bCONR_c(CH_2)_cSO_3R_e$, —$(CH_2)_aNR_bCSNR_c$ $(CH_2)_cSO_3R_e$, —$(CH_2)_aOCONR_e(CH_2)_cSO_3R_e$, —$(CH_2)_aPO_3R_eR_f$, —$(CH_2)_aOPO_3R_eR_f$, —$(CH_2)_a$ $NR_bPO_3R_eR_f$, —$(CH_2)_aCO_2(CH_2)_cPO_3R_eR_f$, —$(CH_2)_a$ $OCO(CH_2)_bPO_3R_eR_f$, —$(CH_2)_aCONR_b(CH_2)_cPO_3R_eR_f$, —$(CH_2)_aNR_bCO(CH_2)_cPO_3R_eR_f$, —$(CH_2)_aNR_bCONR_c$ $(CH_2)_bPO_3R_eR_f$, —$(CH_2)_aNR_bCSNH(CH_2)_cPO_3R_eR_f$, —$(CH_2)_aOCONR_b(CH_2)_cPO_3R_eR_f$ cyano, nitro, halogens, saccharides, hydrophilic peptides, lipophilic peptides, bioactive peptides, proteins, cells, glycopeptides, peptidomimetics, drugs, hormones, metal chelating agents, radioactive and non-radioactive metal complexes, echogenic agents, and arylpolysulfonates; the subscripts a and c independently vary from 1-20, and b vary from 1-100; $R_a$, $R_b$, $R_c$, and $R_d$ are defined in the same manner as $R^1$; $R_e$ and $R_f$ are independently a hydrogen or a negatively-charged group or are defined in the same manner as $R^1$; Bm is any bioactive peptides, proteins, antibodies, antibody fragments, oligosaccharides, drugs, glycomimetics, cells, glycopeptides, peptidomimetics, hormones, metal chelating groups, radioactive and non-radioactive metal complexes, echogenic agents, and the like; each of $R^{10}$, $R^{11}$, and $R^{12}$ may be a hydrophilic or lipophilic linker or a bioactive domain defined in the same manner as Bm, or $R^{10}$ to $R^{12}$ may be combined as a functional unit defined in the same manner as Bm; $R^1$ to $R^9$ are defined in the same manner as Bm, or are independently selected from the group consisting of hydrogen, C1-C20 alkyl, C1-C14 aryl, C1-C20 alkoxyl, C1-20 polyalkoxyalkyl, C1-C20 thioalkyl, C1-C20 carboxyl, C1-20 aminoalkyl, C1-20 hydroxyalkyl, C5-C20 polyhydroxyaryl, carbocyclic, heterocyclic, sulfonate, sulfate, thiol, sulfide, thiother, phosphonate, phosphate, phosphite, carboxylate, amino aryl, cyano, nitro, halogen, saccharide, hydrophilic peptide, lipophilic peptide, bioactive peptide, protein, cells, glycopeptide, peptidomimetic, drug, hormone, metal chelating group, radioactive and non-radioactive metal complex, echogenic agent, arylpolysulfonate, fused aryl, and radioisotope; two or more $R^1$ to $R^9$ may combine to form aromatic derivatives.

The present invention also comprises novel macrocyclic bioconjugate compounds defined as Formula 2:

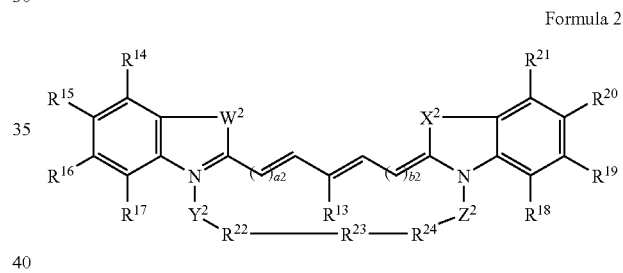

Formula 2 wherein a2 and b2 are defined in the same manner as a1 and b1; $W^2$ and $X^2$ are independently selected from the group consisting of —$CR_aR_b$, —O—, —$NR_b$, —S—, and —Se; $Y^2$ and $Z^2$ are independently selected from the group consisting of —$CR_a$, —C1-10 alkyl, C1-10 aryl, C1-10 alkoxyl, C1-20 polyalkoxyalkyl, C1-10 thioalkyl, C1-10 carboxylic acid, C1-C10 aminoalkyl, C1-10 hydroxyalkyl, C5-C20 polyhydroxyaryl, —$(CH_2)_a$—$NR_a$—, —$CH_2(CH_2$—O—$CH_2)_b$—$CH_2$—O—, —$(CH_2)_a$—$CO_2$—, —$CH_2$—$(CH_2$—O—$CH_2)_b$—$CH_2$—$CO_2$—, —$CH_2$—$(CH_2$—O—$CH_2)_b$—$CH_2$—$NR_a$—, —$(CH_2)_a$—$N(R_b)$—$(CH_2)_c$—$CO_2R_e$, —$(CH_2)_a$—$N(R_b)$—$CH_2$—$(CH_2$—O—$CH_2)_b$—$CH_2$—$CO_2R_e$, —$(CH_2)_a$—$CONR_b$-Bm-, —$CH_2$—$(CH_2$—O—$CH_2)_b$—$CH_2$—$CONR_b$-Bm-, —$(CH_2)_a$—$NR_bCO$-Bm-, —$CH_2$—$(CH_2$—O—$CH_2)_b$—$CH_2NR_bCO$-Bm-, —$(CH_2)_a$—$NR_bCO$-Bm-, —$CH_2$—$(CH_2$—O—$CH_2)_b$—$CH_2NR_bCO$-Bm-, —$(CH_2)_a$—$N(R_b)$—$(CH_2)_c$—$CONR_b$-Bm-, —$(CH_2)_a$—$N(R_b)$—$CH_2$—$(CH_2$—O—$CH_2)_b$—$CH_2$—$CONR_b$-Bm-, —$(CH_2)_aSO_3$—, —$(CH_2)_aS(O)$—, —$(CH_2)_aS$—, —$(CH_2)_aOSO_3$—, —$(CH_2)_aNR_bSO_3$—, —$(CH_2)_aCO_2(CH_2)_bSO_3$—$(CH_2)_aSO_3$—, —$(CH_2)_aOCO$ $(CH_2)_cSO_3$—, —$(CH_2)_aCONR_b(CH_2)_cSO_3$—, —$(CH_2)_aNR_bCO(CH_2)_cSO_3$—, —$(CH_2)_aNR_bCONR_c$ $(CH_2)_cSO_3$—, —$(CH_2)_aNR_bCSNR_c(CH_2)_cSO_3$—, —$(CH_2)_aOCONR_e(CH_2)_cSO_3$—, —$(CH_2)_aPO_3R_e$—, —$(CH_2)_aOPO_3R_e$—, —$(CH_2)_aNR_bPO_3R_e$—, —$(CH_2)_aCO_2$ —(CH$_2$)$_c$PO$_3$R$_e$—, —(CH$_2$)$_a$OCO(CH$_2$)$_b$PO$_3$R$_e$—, —(CH$_2$)$_a$CONR$_b$(CH$_2$)$_c$PO$_3$R$_e$—, —(CH$_2$)$_a$NR$_b$CO (CH$_2$)$_c$PO$_3$R$_e$—, —(CH$_2$)$_a$NR$_b$CONR$_c$(CH$_2$)$_b$PO$_3$R$_e$—, —(CH$_2$)$_a$NR$_b$CSNH(CH$_2$)$_c$PO$_3$R$_e$—, —(CH$_2$)$_a$OCONR$_b$ (CH$_2$)$_c$PO$_3$R$_e$—, cyano, nitro, halogens, saccharides, hydrophilic peptides, lipophilic peptides, bioactive peptides, proteins, cells, glycopeptides, peptidomimetics, drugs, hormones, metal chelating agents, radioactive and non-radioactive metal complexes, echogenic agents, and arylpolysulfonates; the subscripts a and c independently vary from 1-20, and b vary from 1-100; R$_a$, R$_b$, R$_c$, and R$_d$ are defined in the same manner as R$^1$; R$_e$ and R$_f$ are independently a hydrogen or a negatively-charged group or are defined in the same manner as R$^1$; Bm is any bioactive peptides, proteins, antibodies, antibody fragments, oligosaccharides, drugs, glycomimetics, cells, glycopeptides, peptidomimetics, hormones, metal chelating groups, radioactive and non-radioactive metal complexes, echogenic agents, and the like; R$^{13}$ to R$^{21}$ are defined in the same manner as R$^1$ to R$^9$; and R$^{22}$ to R$^{24}$ are defined in the same manner as R$^{10}$ to R$^{12}$.

The present invention further comprises novel macrocyclic bioconjugate compounds defined as Formula 3:

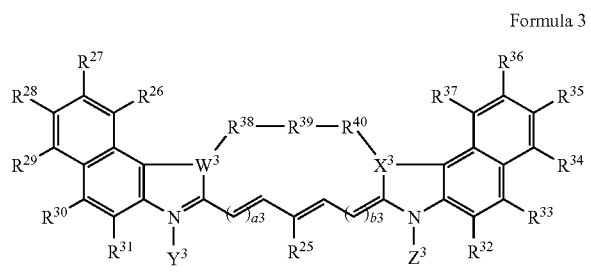

Formula 3 wherein a3 and b3 are defined in the same manner as a1 and b1; W$^3$ and X$^3$ are defined in the same manner as W$^1$ and X$^1$; Y$^3$ and Z$^3$ are defined in the same manner as Y$^1$ and Z$^1$; R$^{25}$ to R$^{37}$ are defined in the same manner as R$^1$ to R$^9$; and R$^{38}$ to R$^{40}$ are defined in the same manner as R$^{10}$ to R$^{12}$.

The present invention also comprises novel macrocyclic bioconjugates defined as Formula 4:

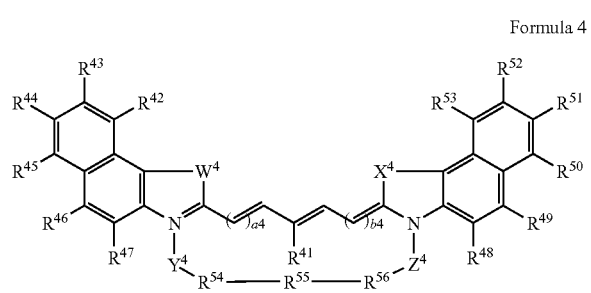

Formula 4 wherein a4 and b4 are defined in the same manner as a1 and b1; W$^4$ and X$^4$ are defined in the same manner as W$^2$ and X$^2$; Y$^4$ and Z$^4$ are defined in the same manner as Y$^2$ and Z$^2$; R$^{41}$ to R$^{53}$ are defined in the same manner as and R$^1$ to R$^9$; and R$^{54}$ to R$^{53}$ are defined in the same manner as R$^{10}$ to R$^{12}$.

The present invention also comprises novel macrocyclic bioconjugate compounds of Formula 5:

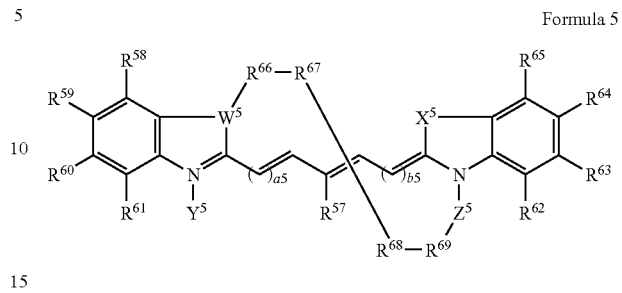

Formula 5 wherein a5 and b5 are defined in the same manner as a1 and b1; W$^5$ is defined in the same manner as W$^1$; X$^5$ is defined in the same manner as X$^2$; Y$^5$ is defined in the same manner as Y$^1$; Z$^5$ is defined in the same manner as Z$^2$; R$^{57}$ to R$^{65}$ are defined in the same manner as and R$^1$ to R$^9$; and R$^{66}$ to R$^{69}$ are defined in the same manner as R$^{10}$ to R$^{12}$.

The present invention also comprises novel macrocyclic bioconjugate compounds of Formula 6:

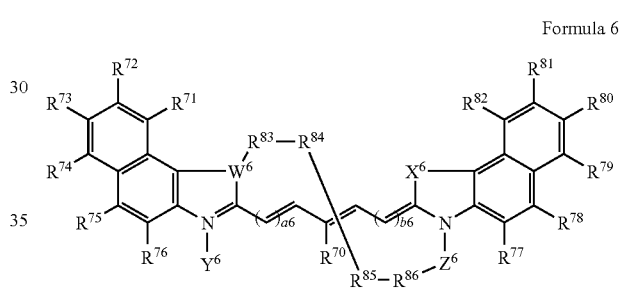

Formula 6 wherein a6 and b6 are defined in the same manner as a1 and b1; W$^6$ is defined in the same manner as W$^1$; X$^6$ is defined in the same manner as X$^2$; Y$^6$ is defined in the same manner as Y$^1$; Z$^8$ is defined in the same manner as Z$^2$; R$^{70}$ to R$^{82}$ are defined in the same manner as R$^1$ to R$^9$; and R$^{83}$ to R$^{86}$ are defined in the same manner as R$^{10}$ to R$^{12}$.

The present invention also comprises novel double crosslinked macrocyclic bioconjugate compounds of Formula 7:

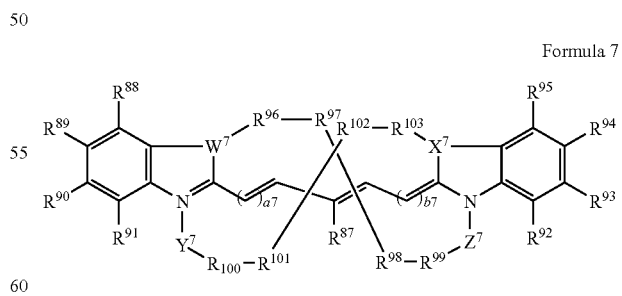

Formula 7 wherein a7 and b7 are defined in the same manner as a1 and b1; W$^7$ and X$^7$ are defined in the same manner as W$^1$ and X$^1$; Y$^7$ and Z$^7$ are defined in the same manner as Y$^2$ and Z$^2$; R$^{87}$ to R$^{95}$ are defined in the same manner as R$^1$ to R$^9$; and R$^{96}$ to R$^{103}$ are defined in the same manner as R$^{10}$ to R$^{12}$.

The present invention also comprises novel double cross-linked macrocyclic bioconjugate compounds of Formula 8:

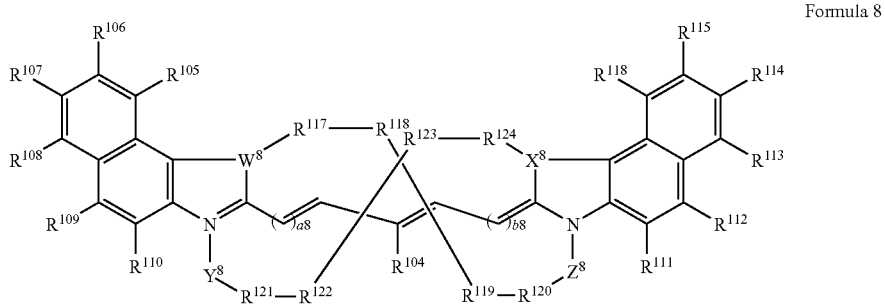

Formula 8 wherein a8 and b8 are defined in the same manner as a1 and b1; $W^8$ and $X^8$ are defined in the same manner as $W^1$ and $X^1$; $Y^8$ and $Z^8$ are defined in the same manner as $Y^2$ and $Z^2$; $R^{104}$ to $R^{116}$ are defined in the same manner as $R^1$ to $R^9$; and $R^{117}$ to $R^{124}$ are defined in the same manner as $R^{10}$ to $R^{12}$.

The present invention also comprises novel double macrocyclic bioconjugate compounds of Formula 9:

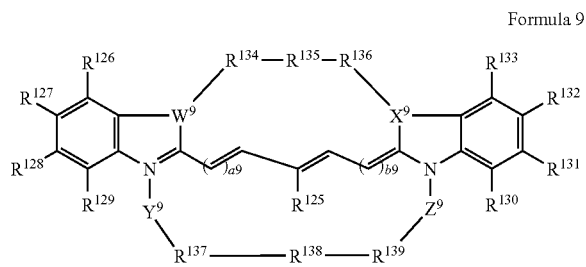

Formula 9 wherein a9 and b9 are defined in the same manner as a1 and b1; $W^9$ and $X^9$ are defined in the same manner as $W^1$ and $X^1$; $Y^9$ and $Z^9$ are defined in the same manner as $Y^2$ and $Z^2$; $R^{125}$ to $R^{133}$ are defined in the same manner as $R^1$ to $R^9$; and $R^{134}$ to $R^{139}$ are defined in the same manner as $R^{10}$ to $R^{12}$.

The present invention also comprises novel double macrocyclic bioconjugate compounds of Formula 10:

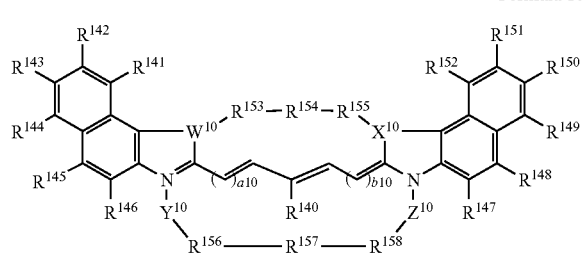

Formula 10 wherein a10 and b10 are defined in the same manner as a1 and b1; $W^{10}$ and $X^{10}$ are defined in the same manner as $W^1$ and $X^1$; $Y^{10}$ and $Z^{10}$ are defined in the same manner as $Y^2$ and $Z^2$; $R^{140}$ to $R^{152}$ are defined in the same manner as $R^1$ to $R^9$; and $R^{153}$ to $R^{158}$ are defined in the same manner as $R^{10}$ to $R^{12}$.

The present invention also comprises novel macrocyclic bioconjugate compounds of Formula 11:

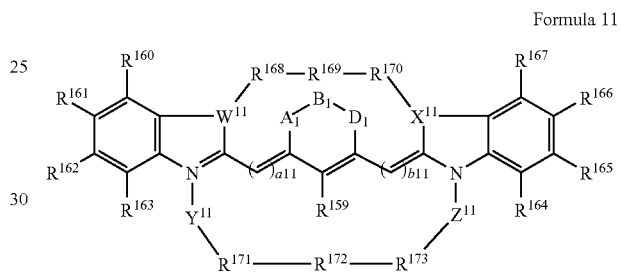

Formula 11 wherein a11 and b11 are defined in the same manner as a1 and b1; $W^{11}$ and $X^{11}$ are defined in the same manner as $W^1$ and $X^1$; $Y^{11}$ and $Z^{11}$ are defined in the same manner as $Y^2$ and $Z^2$; $R^{159}$ to $R^{167}$ are defined in the same manner as $R^1$ to $R^9$; $R^{168}$ to $R^{173}$ are defined in the same manner as $R^{10}$ to $R^{12}$. $A_1$, $B_1$ and $D_1$ are independently selected from the group consisting of —O—, —S—, —Se—, —P—, —$PR_a$—P(O)$R_a$, —S(O)—, —$NR_a$, —$CR_aR_b$—, —C=O, C1-C10 alkyl, C1-C10 aryl, C1-C10 polyhydroxyalkyl, C1-C10 alkoxyl, —CH$_2$(CH$_2$—O—CH$_2$)$_c$—CH$_2$—O—, peptide, —(CH$_2$)$_d$—CO$_2$H, —CH$_2$—(CH$_2$—O—CH$_2$)$_e$—CH$_2$—CO—, —(CH$_2$)$_f$NR$_b$—, and —CH$_2$—(CH$_2$—O—CH$_2$)$_g$—CH$_2$—NR$_b$. $A_1$, $B_1$ and $D_1$ may together form a 5 to 20 membered carbocyclic or heterocyclic ring, optionally containing one or more oxygen, nitrogen, or sulfur atom.

The present invention also comprises novel macrocyclic bioconjugate compounds of Formula 12:

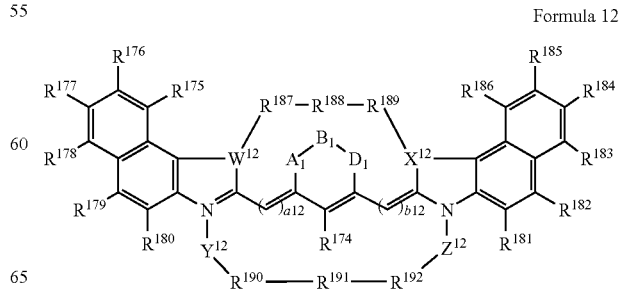

Formula 12 wherein a12 and b12 are defined in the same manner as a1 and b1; $W^{12}$ and $X^{12}$ are defined in the same manner as $W^1$ and $X^1$; $Y^{12}$ and $Z^{12}$ are defined in the same manner as $Y^2$ and $Z^2$; $R^{174}$ to $R^{186}$ are defined in the same manner as $R^1$ to $R^9$; $R^{187}$ to $R^{192}$ are defined in the same manner as $R^{10}$ to $R^{12}$. $A_1$, $B_1$ and $D_1$ are defined in Formula 11.

The present invention also comprises novel macrocyclic bioconjugate compounds of Formula 13:

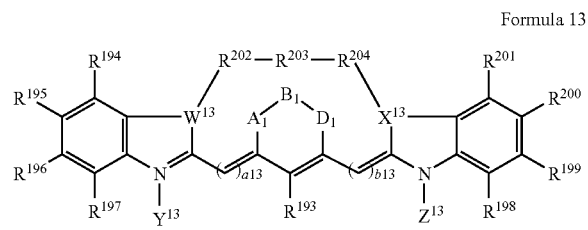

Formula 13 wherein a13 and b13 are defined in the same manner as a1 and b1; $W^{13}$ and $X^{13}$ are defined in the same manner as $W^1$ and $X^1$; $Y^{13}$ and $Z^{13}$ are defined in the same manner as $Y^1$ and $Z^1$; $R^{193}$ to $R^{201}$ are defined in the same manner as $R^1$ to $R^9$; and $R^{202}$ to $R^{204}$ are defined in the same manner as $R^{10}$ to $R^{12}$; $A_1$, $B_1$ and $D_1$ are defined in Formula 12.

The present invention also comprises the novel macrocyclic bioconjugate compounds of Formula 14:

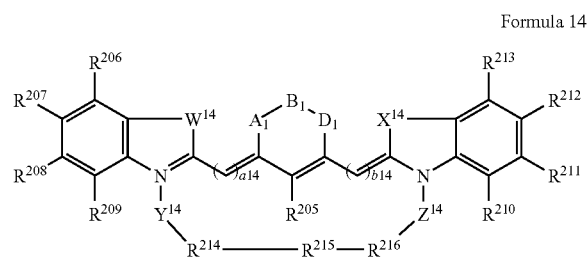

Formula 14 wherein a14 and b14 are defined in the same manner as a1 and b1; $W^{14}$ and $X^{14}$ are defined in the same manner as $W^2$ and $X^2$; $Y^{14}$ and $Z^{14}$ are defined in the same manner as $Y^2$ and $Z^2$; $R^{205}$ to $R^{213}$ are defined in the same manner as and $R^1$ to $R^9$; $R^{214}$ to $R^{216}$ are defined in the same manner as $R^{10}$ to $R^{12}$; $A_1$, $B_1$ and $D_1$ are defined in Formula 11.

The present invention also comprises the novel macrocyclic bioconjugate compounds of Formula 15:

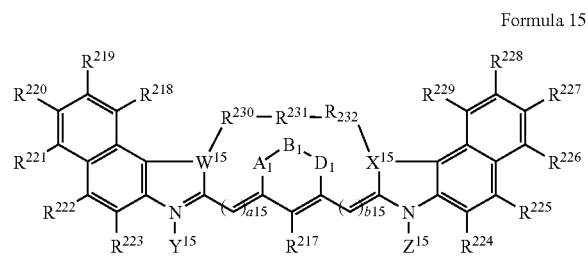

Formula 15 wherein a15 and b15 are defined in the same manner as a1 and b1; $W^{15}$ and $X^{15}$ are defined in the same manner as $W^1$ and $X^1$; $Y^{15}$ and $Z^{15}$ are defined in the same manner as $Y^1$ and $Z^1$; $R^{217}$ to $R^{229}$ are defined in the same manner as $R^1$ to $R^9$; and $R^{230}$ to $R^{232}$ are defined in the same manner as $R^{10}$ to $R^{12}$. $A_1$, $B_1$ and $D_1$ are defined in Formula 11.

The present invention also comprises novel macrocyclic bioconjugate compounds of Formula 16:

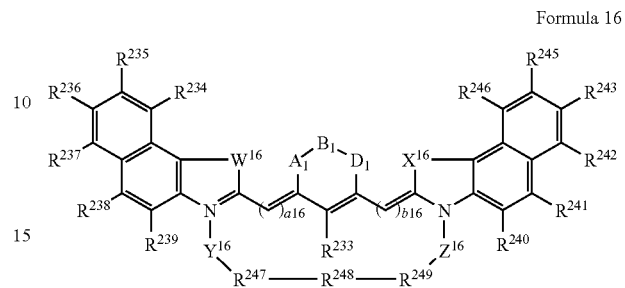

Formula 16 wherein a16 and b16 are defined in the same manner as a1 and b1; $W^{16}$ and $X^{16}$ are defined in the same manner as $W^2$ and $X^2$; $Y^{16}$ and $Z^{16}$ are defined in the same manner as $Y^2$ and $Z^2$; $R^{233}$ to $R^{246}$ are defined in the same manner as and $R^1$ to $R^9$; $R^{247}$ to $R^{249}$ are defined in the same manner as $R^{10}$ to $R^{12}$; $A_1$, $B_1$ and $D_1$ are defined in Formula 12.

The present invention also comprises macrocyclic bioconjugate compounds of Formula 17:

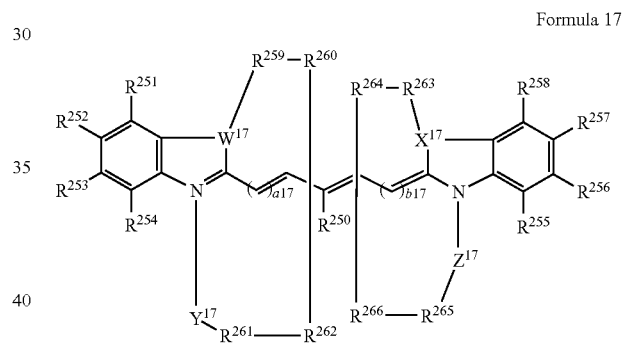

Formula 17 wherein a17 and b17 are defined in the same manner as a1 and b1; $W^{17}$ and $X^{17}$ are defined in the same manner as $W^1$ and $X^1$; $Y^{17}$ and $Z^{17}$ are defined in the same manner as $Y^2$ and $Z^2$; $R^{250}$ to $R^{258}$ are defined in the same manner as $R^1$ to $R^9$; and $R^{259}$ to $R^{265}$ are defined in the same manner as $R^{10}$ to $R^{12}$.

The present invention also comprises novel macrocyclic bioconjugate compounds of Formula 18:

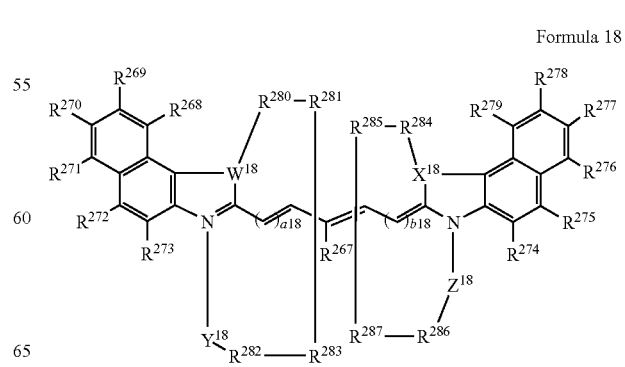

Formula 18 wherein a18 and b18 are defined in the same manner as a1 and b1; $W^{18}$ and $X^{18}$ are defined in the same manner as $W^1$ and $X^1$; $Y^{18}$ and $Z^{18}$ are defined in the same manner as $Y^2$ and $Z^2$; $R^{267}$ to $R^{279}$ are defined in the same manner as $R^1$ to $R^9$; and $R^{280}$ to $R^{286}$ are defined in the same manner as $R^{10}$ to $R^{12}$.

This invention also comprises a method for preparing the compounds of the invention in high yield.

The compounds of this invention allow the emission of light to be quenched by the presence of analytes, including, but not limited to metal ions, pathogens, bacteria, or other organic molecules.

The compounds of the present invention may be employed to quench the emission of light prior to the occurrence of a biological event, is such as enzymatic cleavage of diagnostic bonds, or sequestering into membranes or host molecules.

The structural framework of certain of the compounds of this invention may serve as a scaffold to develop related compounds that have different activity from the parent compounds.

The fluorescence lifetime properties of the compounds of this invention are changed by the macrocyclization synthesis.

The macrocyclic carbocyanine compounds of the present invention can be utilized in the treatment of pathologic conditions by phototherapy. That is, the compound is activated by light through cleavage of labile bonds or generation of free radicals that are cytotoxic to a target microenvironment.

These macrocyclic bioconjugates have been found to exude a robust nature which enables them to have an improved delivery which is more specific to targeted tissue. The robust nature my stem from the rigid cross-links in the chromophore core, i.e. the intramolecular cyclization. The topology of the molecules makes it possible to alter the spectral properties of the compounds by a choice of the ring size. In addition, the linker group from one segment of the molecule to another can beneficially comprise a bioactive segment capable of directing the molecules to their targets.

The compounds described in this invention are stable against exopeptidase degradation inspite of the head-to-tail macrocyclization formulations. Macrocyclization facilitates elucidation of the bioactive conformations of linear peptides, which is useful to optimize the affinity of the compounds for their targets. Compounds that can minimize peptide degradation by exopeptidase and also retain the affinity of the carrier to its receptor is highly unusual.

The present carbocyanine macrocyclic bioconjugates may be inherently excreted by organs other than the liver, such as urinal excretion through the kidneys. But this is not completely understood. The bioconjugates of this invention use hydrophilic units as an integral part of the cyclic chain which may disrupt solvent-induced aggregation in solution.

Herein cyclization has been successfully used as a strategy to improve the binding affinities, selectivities, in vivo stability, and pharmacokinetics of bioactive molecules. The conformational restriction conferred by cyclization facilitates the conformational analysis and bioactive conformation elucidation. In the present invention, the chromophore is flanked by bioactive or chemically useful substituents to achieve the desired molecular or cellular event. Thus, we have disclosed molecular beacons that combine both cyclic and fluorescent features which offer enormous advantages over existing optical probes.

The molecules disclosed can be used in a variety of applications, including detecting and imaging normal and pathophysiologic conditions; monitoring disease status, organ functions, and the efficacy of drugs; performing in vivo, ex-vivo, and in vitro biological and chemical measurements; detecting microorganisms and pathogens; and monitoring or detecting environment pollutants.

DETAILED DESCRIPTION OF THE INVENTION

Figure 1:
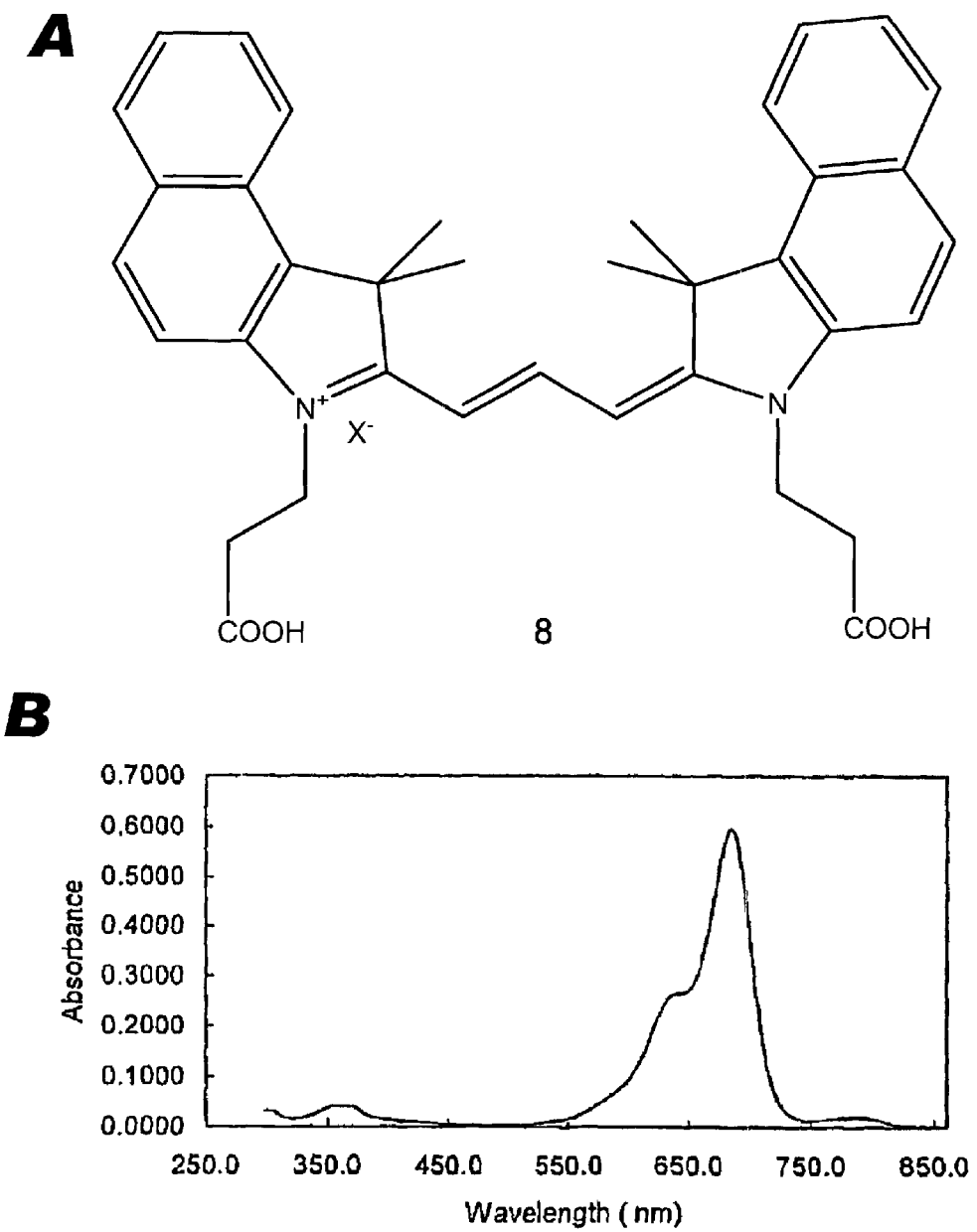
FIG. 1 depicts the (A) structure, (B) UV-Vis spectrum, and (C) emission spectrum of cypate2 (8).
Figure 1C:
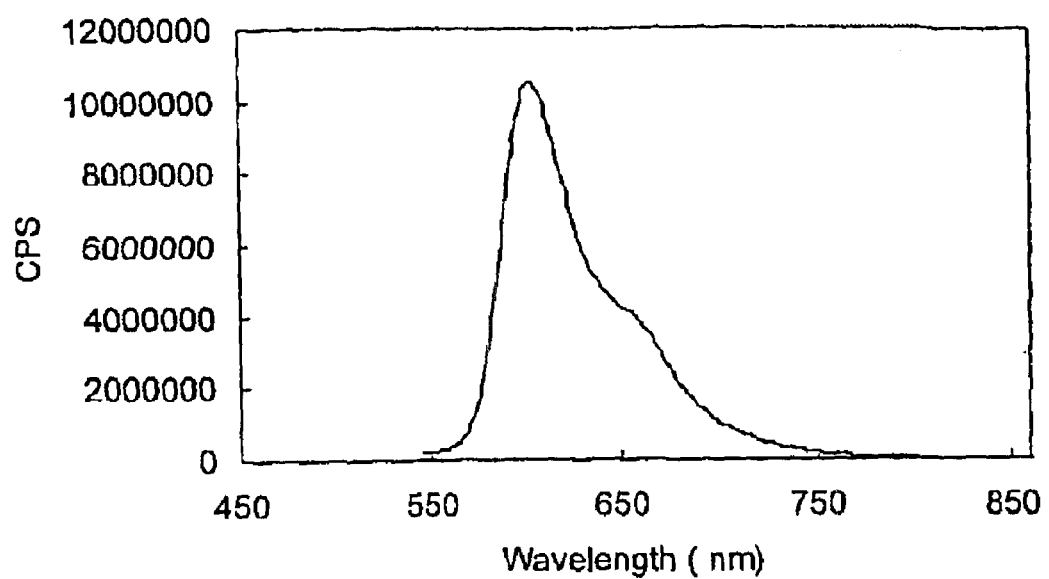

The novel bioconjugate compounds of the present invention comprise compounds of Formulas 1 to 18 and can be prepared from any conventional method. Preferably, one integrates peptide and other bioactive molecules into a fluorescent chromophore core.

The so called macrocyclization or intramolecular linking and cross-linking alters the ring size of molecules to modify the biological characteristics of the bioconjugates, such as changing these bioactive compounds from agonist to antagonist after binding to target a receptor.

Thus, changing the ring size serves as an avenue to alter the agonist or antagonist properties of compounds without drastically changing its structural framework.

Although it is not completely understood, it is believed that increasing the molecular volume transforms the excretion pathway from the size-dependent glomerular filtration mechanism of the kidneys to tubular filtration, which ensures more rapid elimination of the compound from blood plasma. Consequently, imaging can be performed more rapidly after injection of the imaging agent because the target tissue-to-blood ratio of the macrocyclic compounds can be highly concentrated within hours of post injection.

Macrocyclic compounds also have enhanced affinity to different subtypes of target receptors. Optimizing the selectivity of such compounds to the target receptor will minimize the negative effects of the compounds on normal tissue.

As previously stated, changing the macrocyclic ring size can alter the spectral properties of the macrocyclic compounds. This is particularly important for the simultaneous monitoring of two or more physiological processes simultaneously without using widely different compounds. The spatial distribution of the functional groups within the bioconjugate allows those groups to interact with each other, thereby making it possible to completely quench the fluorescence emission by incorporating quenchers in shorter ring structures, such as the addition of metal chelates possessing d-orbital lone pair electrons. This characteristic makes these compounds ideally suited for in vivo and in vitro functional imaging. Particularly, cleavage of one or more amide bonds within the cyclic ring will transform the cyclic chain into a linear analogue that minimizes spatial interaction between the quencher and the chromophore, thereby facilitating the detection of fluorescence emission. The macrocyclic bioconjugate then becomes a highly sensitive probe for detecting the in vivo or in vitro expression of diagnostic enzymes.

The macrocyclic compounds of the present invention, are characterized by a fluorescence lifetime, altered by the macrocyclization, facilitating the use of the macrocyclic compounds as highly sensitive molecular probes in fluorescence lifetime imaging.

The macrocyclic compounds are useful in various biomedical applications including, but not limited to, tomographic imaging of organs; monitoring of organ functions; coronary angiography; fluorescence endoscopy; detection, imaging, and treatment of pathologic conditions; laser guided surgery, photoacoustic and sonofluorescence methods; and the like. Specific embodiments to accomplish some of the aforementioned biomedical applications are given below.

For example, the compounds of the invention are useful in optical tomographic, endoscopic, photoacoustic and sonofluoresence detection and treatment of tumors and other pathologic conditions. They can be employed for localized therapy and imaging.

The compounds when targeting tumors and other abnormalities, can be detected by monitoring the blood clearance profile of the compounds. Alternatively, the compounds serve during laser assisted guided surgery, to detect micrometastases of tumors upon laparoscopy. In yet another aspect of the invention, the bioconjugates of this invention are contrast imaging agents in the diagnosis of atherosclerotic plaques and blood clots; or for monitoring gene or protein expressions; or for phototherapy and multimodal imaging; or nuclear, magnetic resonance, and ultrasound imaging.

In a preferred embodiment, the compounds according to the present invention have the general Formula 1 wherein a1 and b1 vary independently from 0 to 3; $W^1$ and $X^1$ are independently selected from the group consisting of $NR_b$, —$CCH_3$—, $C((CH_2)_aOH)$—, $C((CH_2)_aCO_2H)$—, —$C((CH_2)_aNH_2)$—, and —$C((CH_2)_aNR_aR_b)$; $Y^1$ and $Z^1$ are independently selected from the group consisting of —H, —$CR_aR_b$, —$(CH_2)_a$—$CO_2H$, —$CH_2$—$(CH_2$—O—$CH_2)_b$—$CH_2$—$CO_2H$, —$(CH_2)_a$—$N(R_b)$—$(CH_2)_a$—$CO_2H$, and —$(CH_2)_a$—$N(R_b)$—$CH_2$—$(CH_2$—O—$CH_2)_b$—$CH_2$—$CO_2H$; C1-10 thioalkyl, C1-10 aminoalkyl, C1-10 hydroxyalkyl, —$(CH_2)_a$—CONH-Bm, —$CH_2$—$(CH_2$—O—$CH_2)_b$—$CH_2$—CONH-Bm, —$(CH_2)_aSO_3^-$, —$(CH_2)_aOPO_3^-$, monosaccharides, disaccharides, metal chelating agents, peptides, proteins, radioactive and non-radioactive metal complexes; the subscripts a and c vary independently from 1 to 3; and b varies from 1 to 50.

In another preferred embodiment, the compounds according to the present invention have the general Formula 2 wherein a2 and b2 vary independently from 0 to 3; $W^2$ and $X^2$ are independently selected from the group consisting of —$C(CH_3)_2$, $C((CH_2)_aOH)CH_3$, $C((CH_2)_aOH)_2$, $C((CH_2)_aCO_2H)CH_3$, $C((CH_2)_aCO_2H)_2$, $C((CH_2)_aCONHR_b)CH_3$, $C((CH_2)_aCONHR_b)_2$, $C((CH_2)_aNH_2)CH_3$, $C((CH_2)_aNH_2)_2$, $C((CH_2)_aNR_aR_b)CH_3$, $C((CH_2)_aNR_aR_b)_2$; —O—, —$NR_b$, and —S—; $Y^2$ and $Z^2$ are independently selected from the group consisting of —$C(CH_3)$—, $C(CH_2)_aOH)$—, $C(CH_2)_aOR_a)$—, $C((CH_2)_aCO_2H)$—, $C(CH_2)_aCOR_a)$—, $C((CH_2)_aCONHR_b)$—, $C(CH_2)_aNH_2)$—, $C(CH_2)_aNR_aR_b)$—, $C(CH_2)_aOH)$—$(CH_2)_aCO$—, $C((CH_2)_aOR_a)$$(CH_2)_aO$—, $C(CH_2)_aCOR_a)$—$(CH_2)_aNH$—, $C((CH_2)_aCONHR_b)$—, $C((CH_2)_aNH_2)$—, $C((CH_2)_aNR_aR_b)$—, —C1-5 alkyl, C1-10 aryl, C1-10 alkoxyl, C1-6 carboxyl, C1-7 aminoalkyl, —$(CH_2)_a$—$NR_a$—, —$CH_2(CH_2$—O—$CH_2)_b$—$CH_2$—O—, —$(CH_2)_a$—$CO_2$—, —$CH_2$—$(CH_2$—O—$CH_2)_b$—$CH_2$—$CO_2$—, —$CH_2$—$(CH_2$—O—$CH_2)_b$—$CH_2$—$NR_a$—, —$(CH_2)_a$—NHCO-Bm-, —$CH_2$—$(CH_2$—O—$CH_2)_b$—$CH_2$—$NR_b$CO-Bm, —$(CH_2)_a$—$N(R_b)$—$CH_2$—$(CH_2$—O—$CH_2)_b$—$CH_2$—$CONR_b$-Bm-, monosaccharides, disaccharides, metal chelating agents, peptides, proteins, radioactive and non-radioactive metal complexes; the subscripts a and c vary independently from 1 to 3; and b varies from 1 to 50.

In another preferred embodiment, the compounds according to the present invention have the general Formula 3 wherein a3 and b3 vary independently from 0 to 3; $W^3$ and $X^3$ are independently selected from the group consisting of $NR_b$, —$CCH_3$—, $C((CH_2)_aOH)$—, $C((CH_2)_aCO_2H)$—, —$C((CH_2)_aNH_2)$—, and —$C((CH_2)_aNR_aR_b)$; $Y^3$ and $Z^3$ are independently selected from the group consisting of —H, —$CR_aR_b$, —$(CH_2)_a$—$CO_2H$, —$CH_2$—$(CH_2$—O—$CH_2)_b$—$CH_2$—$CO_2H$, —$(CH_2)_a$—$N(R_b)$—$(CH_2)_a$—$CO_2H$, and —$(CH_2)_a$—$N(R_b)$—$CH_2$—$(CH_2$—O—$CH_2)_b$—$CH_2$—$CO_2H$; C1-10 thioalkyl, C1-C10 aminoalkyl, C1-C10 hydroxyalkyl, —$(CH_2)_a$—CONH-Bm, —$CH_2$—$(CH_2$—O—$CH_2)_b$—$CH_2$—CONH-Bm, —$(CH_2)_aSO_3^-$, —$(CH_2)_aOPO_3^-$, monosaccharides, disaccharides, metal chelating agents, peptides, proteins, radioactive and non-radioactive metal complexes; the subscripts a and c vary independently from 1 to 3; and b varies from 1 to 50.

In another preferred embodiment, the compounds according to the present invention have the general Formula 4 wherein a4 and b4 vary independently from 0 to 3; $W^4$ and $X^4$ are independently selected from the group consisting of —$C(CH_3)_2$, $C((CH_2)_aOH)CH_3$, $C((CH_2)_aOH)_2$, $C((CH_2)_aCO_2H)CH_3$, $C((CH_2)_aCO_2H)_2$, $C((CH_2)_aCONHR_b)CH_3$, $C((CH_2)_aCONHR_b)_2$, $C((CH_2)_aNH_2)CH_3$, $C((CH_2)_aNH_2)_2$, $C((CH_2)_aNR_aR_b)CH_3$, $C((CH_2)_aNR_aR_b)_2$; —O—, —$NR_b$, and —S—; $Y^4$ and $Z^4$ are independently selected from the group consisting of —$C(CH_3)$—, $C(CH_2)_aOH)$—, $C(CH_2)_aOR_a)$—, $C((CH_2)_aCO_2H)$—, $C(CH_2)_aCOR_a)$—, $C((CH_2)_aCONHR_b)$—, $C(CH_2)_aNH_2)$—, $C(CH_2)_aNR_aR_b)$—, $C(CH_2)_aOH)$—$(CH_2)_aCO$—, $C((CH_2)_aOR_a)$$(CH_2)_aO$—, $C(CH_2)_aCOR_a)$—$(CH_2)_aNH$—, $C((CH_2)_aCONHR_b)$—, $C((CH_2)_aNH_2)$—, $C((CH_2)_aNR_aR_b)$—, C1-5 alkyl, C1-10 aryl, C1-10 alkoxyl, C1-6 carboxyl, C1-C7 aminoalkyl, —$(CH_2)_a$—$NR_a$—, —$CH_2(CH_2$—O—$CH_2)_b$—$CH_2$—O—, —$(CH_2)_a$—$CO_2$—, —$CH_2$—$(CH_2$—O—$CH_2)_b$—$CH_2$—$CO_2$—, —$CH_2$—$(CH_2$—O—$CH_2)_b$—$CH_2$—$NR_a$—, —$(CH_2)_a$—NHCO-Bm-, —$CH_2$—$(CH_2$—O—$CH_2)_b$—$CH_2NR_b$CO-Bm, —$(CH_2)_a$—$N(R_b)$—$CH_2$—$(CH_2$—O—$CH_2)_b$—$CH_2$—$CONR_b$-Bm-, monosaccharides, disaccharides, metal chelating agents, peptides, proteins, radioactive and non-radioactive metal complexes; the subscripts a and c vary independently from 1 to 3; and b varies from 1 to 50.

In particularly preferred embodiment of the invention, the bioconjugates according to Formulas 1, 2, 3, and 4 have a1 and a2, b1 and b2 being 3 and $R^1$ to $R^9$ and those defined in the same manner as $R^1$ and $R^9$ being hydrogen, and where Bm is selected from RGD peptide derivatives, i.e. those having arginine, glycine, and aspartic acid peptide sequence.

In a preferred embodiment, the methods of the invention utilize light of a wavelength in the region of 350-1300 nm.

In a preferred embodiment, a therapeutic procedure comprises attaching a porphyrin to a bioconjugate and using it for photodynamic therapy or shining light of a specific wavelength on the dipeptide conjugate of this invention to achieve a photodynamic therapy effect.

The bioconjugates of the invention can be formulated into diagnostic compositions for enteral or parenteral administration. These compositions contain an effective amount of the compound along with conventional pharmaceutical carriers and excipients appropriate for the type of administration contemplated. For example, parenteral formulations advantageously contain a sterile aqueous solution or suspension of compounds according to this invention. Parenteral compositions may be injected directly or mixed with a large volume parenteral composition for systemic administration. Such parenteral solutions also may contain pharmaceutically acceptable buffers and, optionally, electrolytes such as sodium chloride. Compositions for enteral administration may vary widely, as is well known in the art. In general, such formulations are liquids which include an effective amount of the compound in aqueous solution or suspension. Such enteral compositions may optionally include buffers, surfactants, thixotropic agents, and the like. Compositions for oral administration may also contain flavoring agents and other ingredients for enhancing their organoleptic qualities.

Diagnostic compositions continuing compounds of this invention are administered in doses effective to achieve the desired enhancement. Such doses may vary widely, depending upon the particular compound employed, the organs or tissues which are the subject of the imaging procedure, the imaging equipment being used, and the like. The diagnostic compositions of the invention are used in the conventional manner. The compositions may be administered to a patient, typically a warm-blooded animal, either systemically or locally to the organ or tissue to be imaged, and the patient then subjected to the imaging procedure.

Combinations of the above described compounds, compositions and uses also represent important approaches to the synthesis and use of carbocyanine compounds with a variety of photophysical and chemical properties for the biomedical advancements of this invention.

The present invention is further detailed in the following Examples, which are offered by way of illustration and are not intended to limit the scope of the invention in any manner.

EXAMPLE 1

Synthesis of 1,1,2-trimethyl[1H]-benz[e]indole-3-propanoic acid (1)

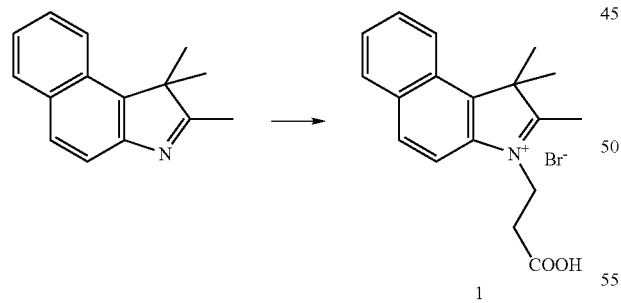

A mixture of 1,1,2-trimethyl-[1H]-benz[e]indole (10.0 g, 47.8 mmol) and 3-bromopropanoic acid (7.3 g, 47.8 mmol) in 1,2-dichlorobenzene (50 mL) was heated with stirring at 110° c. for 18 h. After the resulting mixture was cooled to room temperature, the precipitated was collected by filtration, triturated with DCM thoroughly, and dried under vacuum to afford 15.2 g of light brown powder (88%). ESI-MS: observed for [MH]$^+$ 281.31.

EXAMPLE 2

Synthesis of Bispropylcarboxymethylindocyanine Dye Via Pre-acetylation (Cypate, 2)

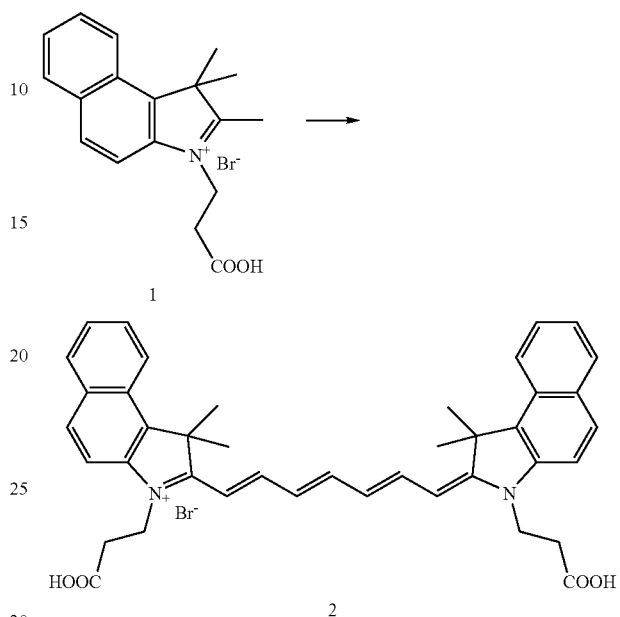

A solution of Ac$_2$O (1.20 g, 11.75 mmol) in DCM (5 mL) was added drop-wise to a cooled, stirring suspension of glutaconaldehyde dianilide monohydrochloride (2.84 g, 9.97 mmol) and DIEA (2.60 g, 20.11 mmol) in DCM (20 mL). The resulting clear solution was stirred for another 1 h and concentrated. The residue was dissolved in methanol (5.0 mL) was added drop-wise to a refluxing solution of 1 (10.0 g, 27.62 mmol) and sodium acetate (3.9 g, 47.54 mmol) in methanol (50 mL). The mixture was refluxed for another 16 h and concentrated. The residue was washed with ethyl acetate, 5% HCl solution, and ethyl acetate. The crude product was further purified by re-crystallization from acetonitrile/water (3:7) to afford 4.3 g (61%). ESI-MS: observed for [MH]$^+$ 625.34.

EXAMPLE 3

Synthesis of Symmetrical Dyes at Room Temperature

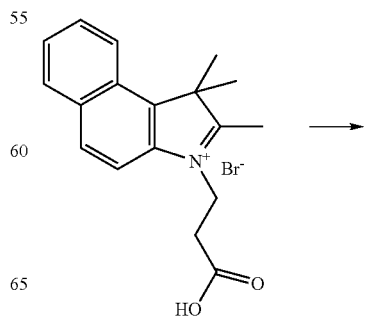

-continued

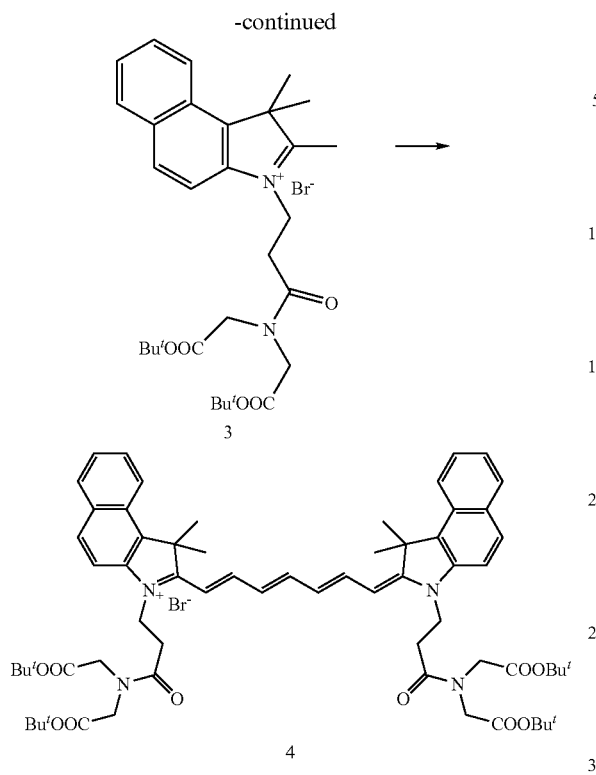

To a stirred and cooled solution of 1 (7.2 g, 19.87 mmol), di-tertbutyl iminodiacetate (6.0 g, 24.46 mmol), and HOBT (2.68 g, 19.85 mmol) in DMF was added EDCI (4.5 g, 23.47 mmol). The mixture was stirred for 3 h and concentrated. The residue was dissolved in DCM (50 mL), washed with 5% HCl solution, 5% NaHCO₃, brine, and dried over Na₂SO₄. Purification by flash column chromatography afforded 3 (7.0 g, 60%).

A solution of Ac₂O (67 mg) in DCM (5 mL) was added drop-wise to a cooled, stirring suspension of glutaconaldehyde dianilide monohydrochloride (60 mg, 0.21 mmol) and TEA (67 mg, 0.66 mmol) in DCM (5 mL), stirred for 10 min. To the resulting clear solution was added a solution of 3 (300 mg, 0.51 mmol) and TEA (52 mg) in DCM (5 mL). The mixture was stirred at room temperature for 72 h, washed with 5% HCl solution, 5% NaHCO₃ solution, and brine, filtered, and concentrated. The crude product was further purified by flash column chromatography to afford the desired product 4 (158 mg, 65%). ESI-MS: observed for [MH]⁺ 1079.49.

EXAMPLE 4

Synthesis of Unsymmetrical Dyes Via Benzolate Intermediate

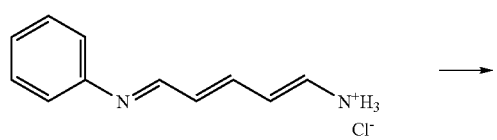

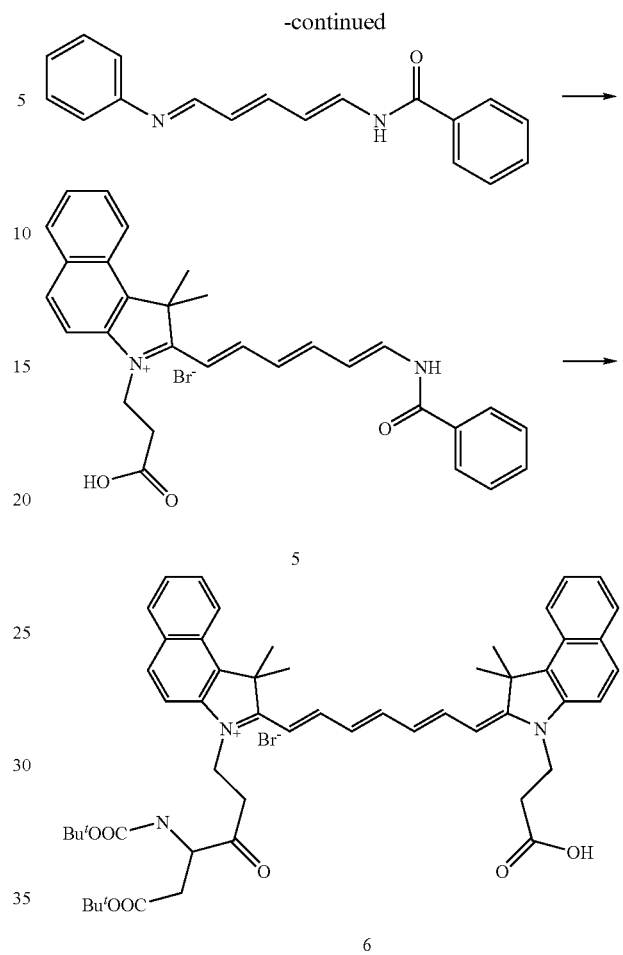

A solution of benzoyl chloride (17 mg, 0.12 mmol) in DCM (5 mL) was added drop-wise to a cooled, stirring suspension of glutaconaldehyde dianilide monohydrochloride (28 mg, 0.10 mmol) and DIEA (30 mg, 0.3 mmol) in DCM (5 mL). The resulting clear solution was stirred for another 2 h and was added dropwise into a solution of 1 (30 mg, 0.083 mmol). The mixture was stirred for overnight, followed by adding 3 (70.7 mg, 0.12 mmol). The mixture was refluxed for 12 h, washed with 5% CHl solution, H₂O, and brine, dried over Na₂SO₄, filtered, and concentrated. Purification by flash column chromatography afforded 6 (32.6 mg, 35%). ES-MS: [MH]⁺ 852.41.

EXAMPLE 5

Synthesis of Cypate3 (7)

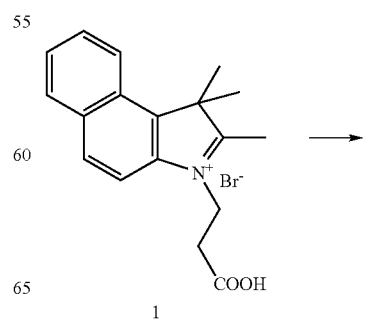

-continued

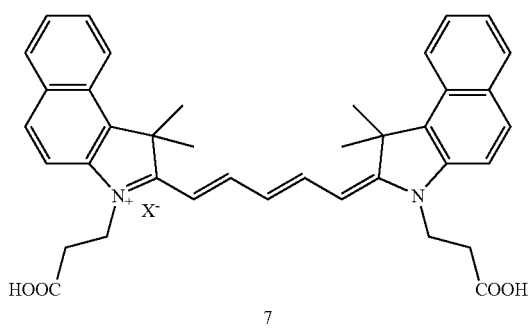

7

Cypate3 was similarly prepared from malconaldehyde dianil monohydrochloride by using the procedure described above for 2. The crude product was further purified by re-crystallization with 30% aqueous acetonitrile and dried to afford 3.2 g (~60%). Observed for [MH]$^+$, 599.32.

EXAMPLE 6

Synthesis of Cypate2 (8)

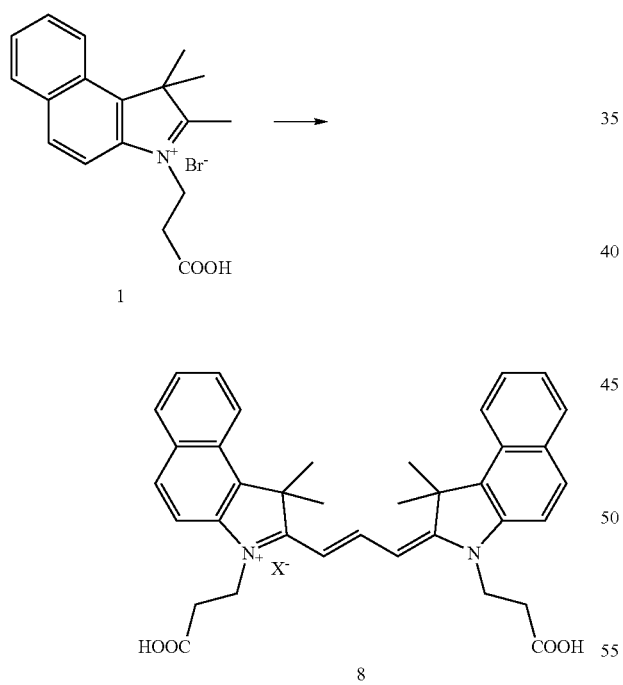

A mixture of HC(OC$_2$H$_5$)$_3$ (74.1 mg) and 1 (362.0 mg, 1.0 mmol), 2,6-lutidine (215 mg) in ethanol (20 mL) was heated with stirring at 100° C. for 3 h. The solvent was removed by evaporation and washed with ether and 10% hydrochloric acid solution and the crude product was re-crystallized from CH$_3$CN/H$_2$O to afford 8 (140 mg, 43%). Observed for [MH]$^+$, 573.41.

EXAMPLE 7

Synthesis of Cyclic Cypate-Lys Conjugate (9)

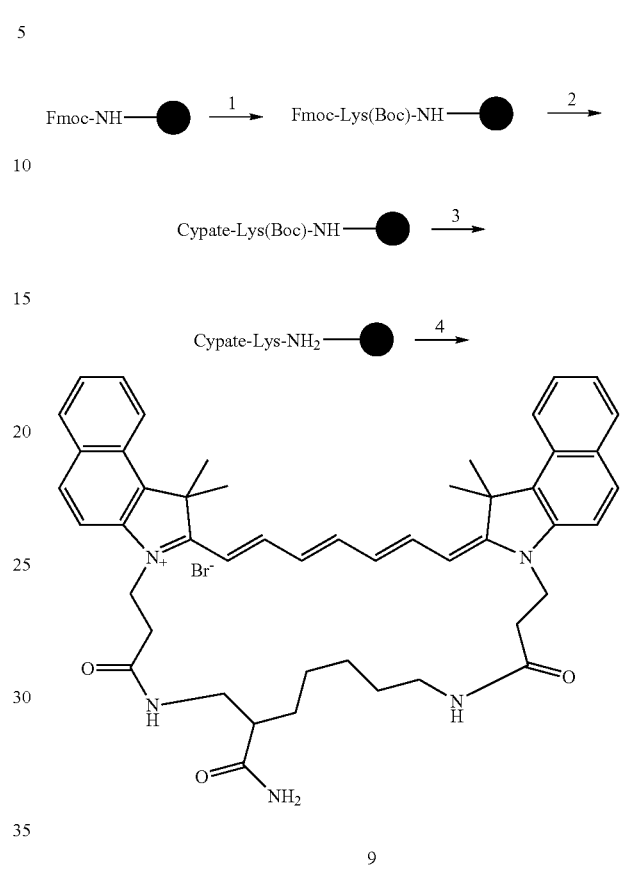

9

Fmoc-Lys was attached to Rink amide resin (60 mg, 0.0366 mmol) and the Fmoc was deprotected by piperidine in DMF (20%). A solution of Cypate(129 mg, 5 equiv), HOBT(24.7 mg), and DIC (11.5 mg, 2.5 equiv) in DMF (3 mL) was added into the resin and swirled overnight. After filtered, the resin was washed with DMF and DCM, cleaved with TFA/H2O (95:5) for 3 h, filtered, concentrated, and dried. The crude product was dissolved in 20 mL DCM and added dropwise into a stirred solution of PyBOP (38 mg), HOBT (9.9 mg), and DIEA (18.9 mg) in DCM/DMF(195:5, 200 mL) and the resulting mixture was stirred overnight, concentrated, and purified by HPLC to afforded 1.5 mg of the desired product.

EXAMPLE 8

Synthesis of Cyclic Cypate-tripetide Conjugate (11)

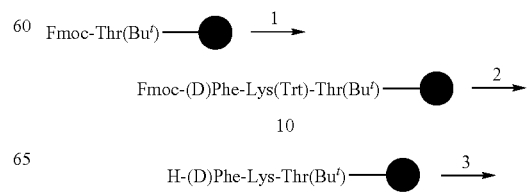

-continued

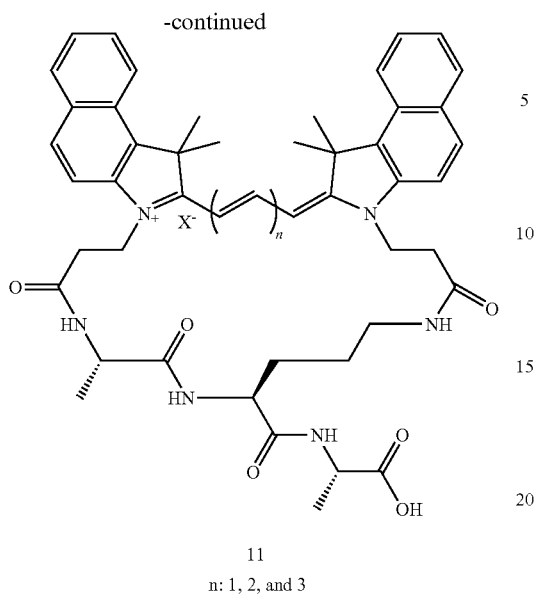

11
n: 1, 2, and 3

The resin-bound tripeptide 10 was assembled from Fmoc-Thr(But)-Wang resin (0.61 mmol/g, 60 mg) using the conventional Fmoc chemistry. The obtained resin was deblocked first by piperidine, followed by the removal of the trityl group of Lys using a solution of TFA and TIS in DCM (1:5:94). After the resin was washed thoroughly with a solution of DIEA in DMF (10%) and DMF, a mixture of 2 (38.7 mg, 0.055 mmol), HOBT (14.8 mg, 0.11 mmol), and DIC (14 mg, 0.11 mmol) in DMF was added into the resin and the mixture was swirled overnight, filtered, washed with DMF, DCM, and cleaved with TFA/H$_2$O (95:5) for 3 h, concentrated, and dried. Purification by HPLC afforded 11 (2.3 mg).

EXAMPLE 9

Synthesis of Cyclic Cypate-tetrapeptide Conjugate (12)

Fmoc-Thr(Bu$^t$)—● $\xrightarrow{1}$

Fmoc-Ala-(D)Phe-Lys(Dde)-Thr(Bu$^t$)—● $\xrightarrow{2}$

-continued

H-Ala-(D)Phe-Lys-Thr(Bu$^t$)—● $\xrightarrow{3}$

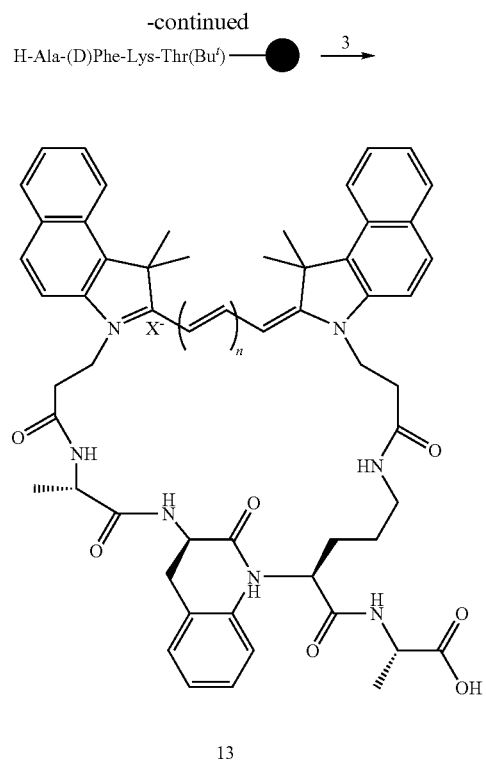

13
n: 1, 2, and 3

The resin-bound tetrapeptide was assembled from Fmoc-Thr(But)-Wang resin (60 mg, 0.61 mmol/g) using conventional Fmoc chemistry. The Fmoc and Dde protecting groups were deprotected by piperidine/DMF(20%) and 2% hydrazine/DMF, respectively. After washed with DMF, DIEA in DMF solution (10%), CH$_3$OH, and DMF, the resin was swirled with a solution of 2 (38.7 mg, 0.055 mmol), HOBT (14.8 mg, 0.11 mmol), and DIC (14 mg, 0.11 mmol) overnight. The resin was filtered, and washed with DMF, CH$_3$OH, and DCM, cleavaged with TFA/H2O (95:5) for 1 h. The product was obtained by HPLC purification (3.45 mg).

EXAMPLE 10

Synthesis of Cyclic Cypate-hexapeptide Conjugate (10)

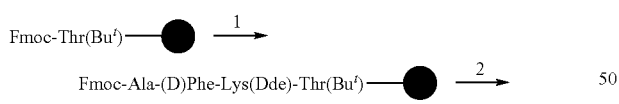

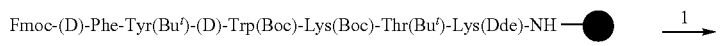

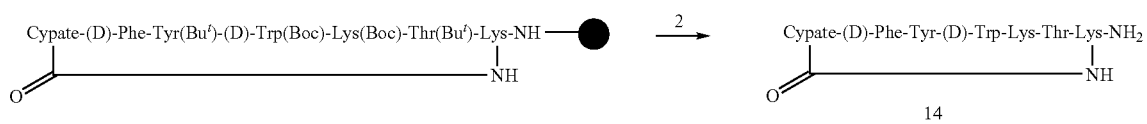

14

The title compound 14 was prepared similarly from Rink amide resin (250 mg, 0.15 mmol) using the procedure described for 13. 3.1 mg of 15 was obtained.

EXAMPLE 11

Synthesis of Cyclic Cypate-nonapeptide Conjugate (15)

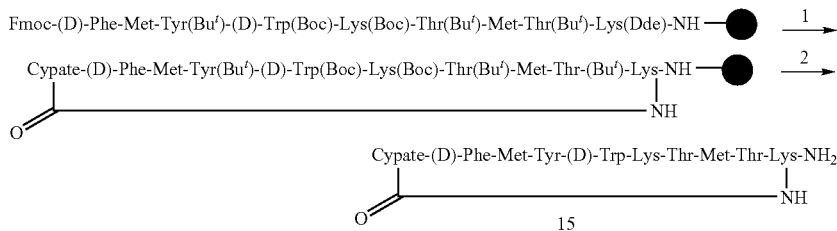

The title compound 15 was prepared similarly from Rink amide resin (0.25 mg, 0.15 mmol) using the procedure described for 13. 2.5 mg of 15 was obtained.

EXAMPLE 12

Synthesis of Cyclic Cypate-Bombesin Conjugate (16)

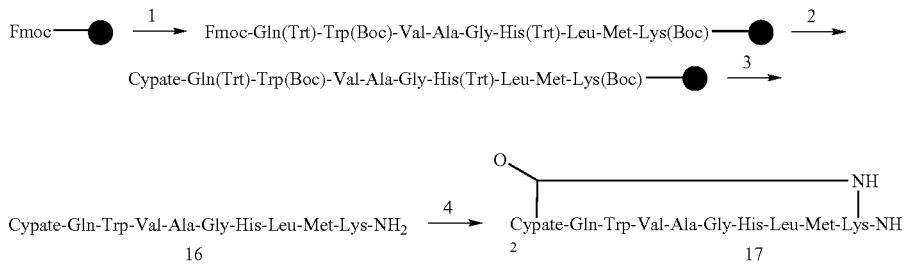

The resin-bound bombesin analog, i.e. Fmoc-Gln(Trt)-Trp(Boc)-Val-Ala-Gly-His(Trt)-Leu-Met-Lys(Boc)-Rink-Amide (SEQ ID NO: 1)resin was assembled from Rink amide-resin (50 mg, 0.031 mmol) based on the conventional Fmoc chemistry. (Peptides shown above are disclosed as SEQ ID NOS 1 and 2 respectively). After the N-terminal Fmoc was removed by piperidine in DMF (20%), a solution of Cypate (211.5 mg, 0.3 mmol), HOBT (40.5 mg, 0.30 mmol), DIC (126.0 mg, 0.1 mmol) was added. The resulting mixture was swirled overnight at room temperature. The resin was washed with DMF and DCM, cleaved with a TFA solution s (TFA: Phenol:thioanisole:water v:v 85:5:5:5, 4 ml) (2 h), and concentrated. The product was precipitated in cooled tert-butyl methyl ether to afford 2.8 mg of the crude intermediate 16.

A solution of 30 mg of 16 in DMF (5 mL) was added dropwise into a solution of PyBOP (26.7 mg), HOBT (7.0 mg), and DIEA (25 mg) in DCM (300 mL) containing 10 ml of DMF. The mixture was stirred overnight, concentrated, and purified by HPLC to afforded 16 (8 mg, 27%). ESI-MS: $[MH]^+$ 1657.69, $[MH_2]^{2+}$ 829.47

EXAMPLE 13

Synthesis of Cyclic Cypate-Octreotide Conjugate (18)

-continued

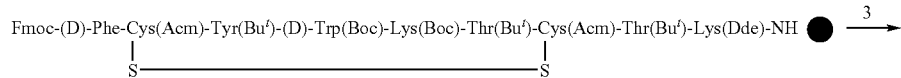

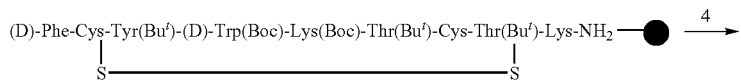

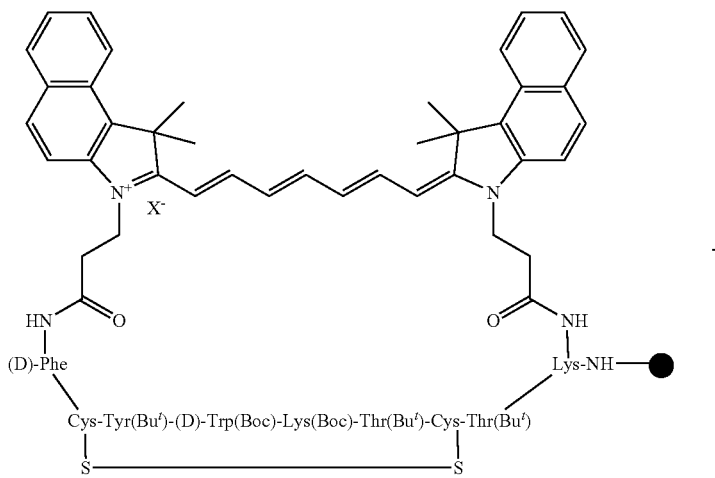

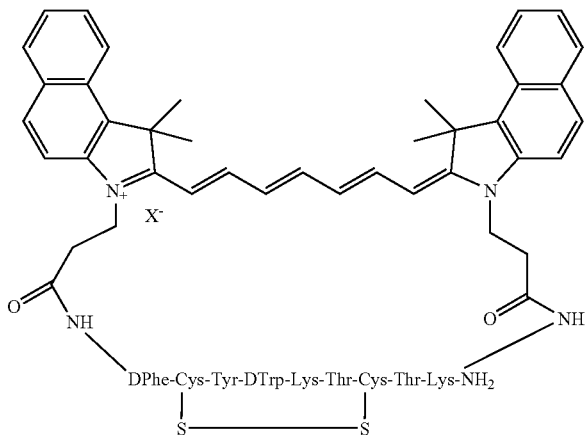

18

The resin-bound peptide, i.e. Fmoc-dF-C(Acm)-Y(But)-dW(Boc)-K(Boc)-T(But)-C(Acm)-T(But)-K(Dde)-NH-Resin were assembled starting from Rink amide-resin (50 mg, 0.061 mmol/g) based on the conventional Fmoc chemistry. Typically, each synthetic cycle consisted of (i) a 20-min deprotection with 20% piperidine in DMF, (ii) coupling with a solution of Fmoc-amino acid (2 equiv), HBTU (2 equiv), HOBT (2 equiv), and DIEA (4 equiv) in DMF (5 mL) for 2 h. As monitored by the ninhydrin test, single coupling of one hour was usually complete. After the sequence assembly was finished, the linear peptide was treated with thallium(III) trifluoroacetate (2.0 equiv) in DMF for 1.5 h to form the disulfide bond, followed by Fmoc deprotecton (using 20% piperidine), and washed with DMF and DCM, and Dde deprotection (using 2% hydrazine solution in DMF for 3 min (3 mL×3), and washed with DMF, $CH_3OH$, 2% DIEA in DMF, and DMF. To the resulting resin-bound peptide was added a solution of Cypate (22.0 mg, 0.03 mmol), HOBT (8.1 mg, 0.06 mmol), PyBOP (39.0 mg, 0.075 mmol) and DIEA (15.5 mg, 0.12 mmol) in DMF (2.5 mL). The resulting mixture was agitated for 5 h at room temperature. The resin was washed with DMF and DCM, cleaved with a TFA solution (TFA:Phenol:thioanisole:water v:v 85:5:5:5, 4 ml), and concentrated. The product was precipitated in cooled tert-butyl methyl ether and purified by semi-preparative HPLC to afford 2.8 mg in a yield of 4%. Analytical HPLC RT=17.13 min; ESI-MS: observed for $[MH_2]^+$ 883.5 and $[MH]^+$ 1765.7.

EXAMPLE 14

Synthesis of Cyclic Cypate3-Octreotide Conjugate (19)

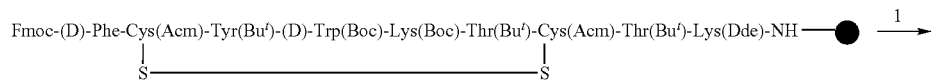

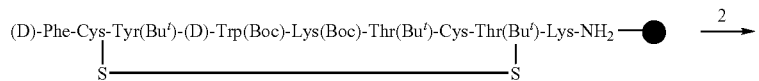

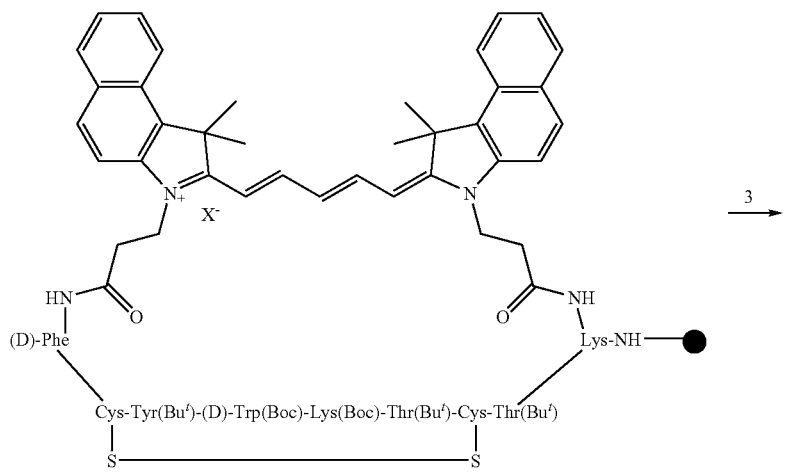

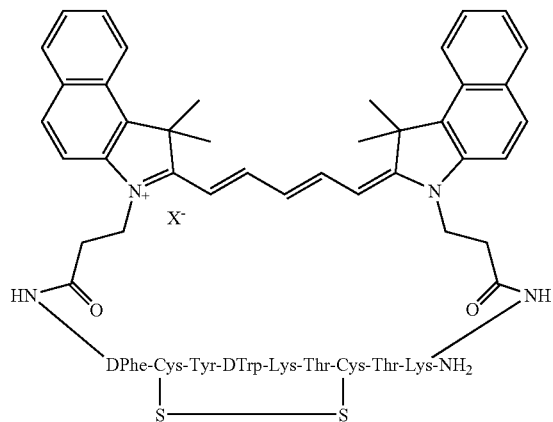

19

Reagents and conditions: 1. peptide assembly using conventional Fmoc chemistry: a. Piperidine/DMF (20%); b. Fmoc-AA/HOBT/HBTU/DIEA/DMF; 2. thallium trifluoroacetate/DMF; 3. a. Piperidine/DMF (20%); b. hydrazine/DMF(2%); c. Cypate3/HOBT/DIC, 24 h; d. trifluoroacetic acid/water/phenol/thioanisole(85:5:5:5), 3 h.

Preparation of this title compound was performed from Fmoc-Protected Octreotide peptide—Wang resin by the same procedure described in Example 13 using Cypate3 (7) instead of Cypate4 (2).

EXAMPLE 15

Synthesis of Cyclic Cypate2-Octreotide Conjugate (20)

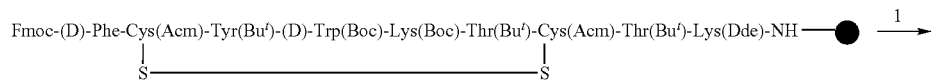

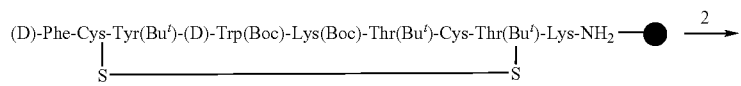

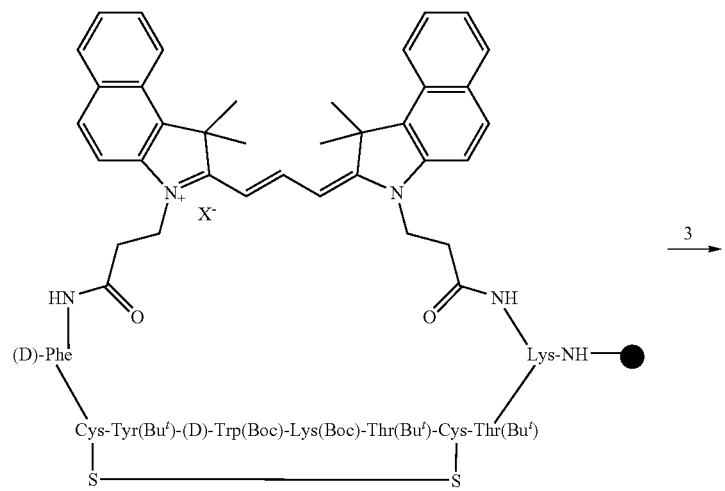

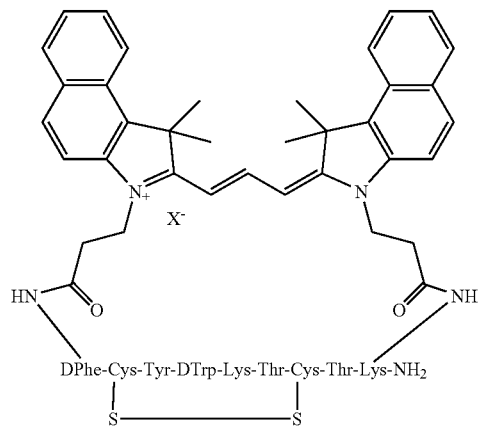

20

Reagents and conditions: 1. peptide assembly using conventional Fmoc chemistry: a. Piperidine/DMF (20%); b. Fmoc-AA/HOBT/HBTU/DIEA/DMF; 2. thallium trifluoroacetate/DMF; 3. a. Piperidine/DMF (20%); b. hydrazine/DMF(2%); c. Cypate2/HOBT/DIC, 24 h; d. trifluoroacetic acid/water/phenol/thioanisole(85:5:5:5), 3 h.

Preparation of this title compound was performed from Fmoc-Protected Octreotide peptide—Wang resin by the same procedure described in Example 13 using Cypate2 (8) instead of Cypate4 (2).

EXAMPLE 16
Synthesis of Substituted Cypate4 (21) and its Octreotide Conjugate (22)
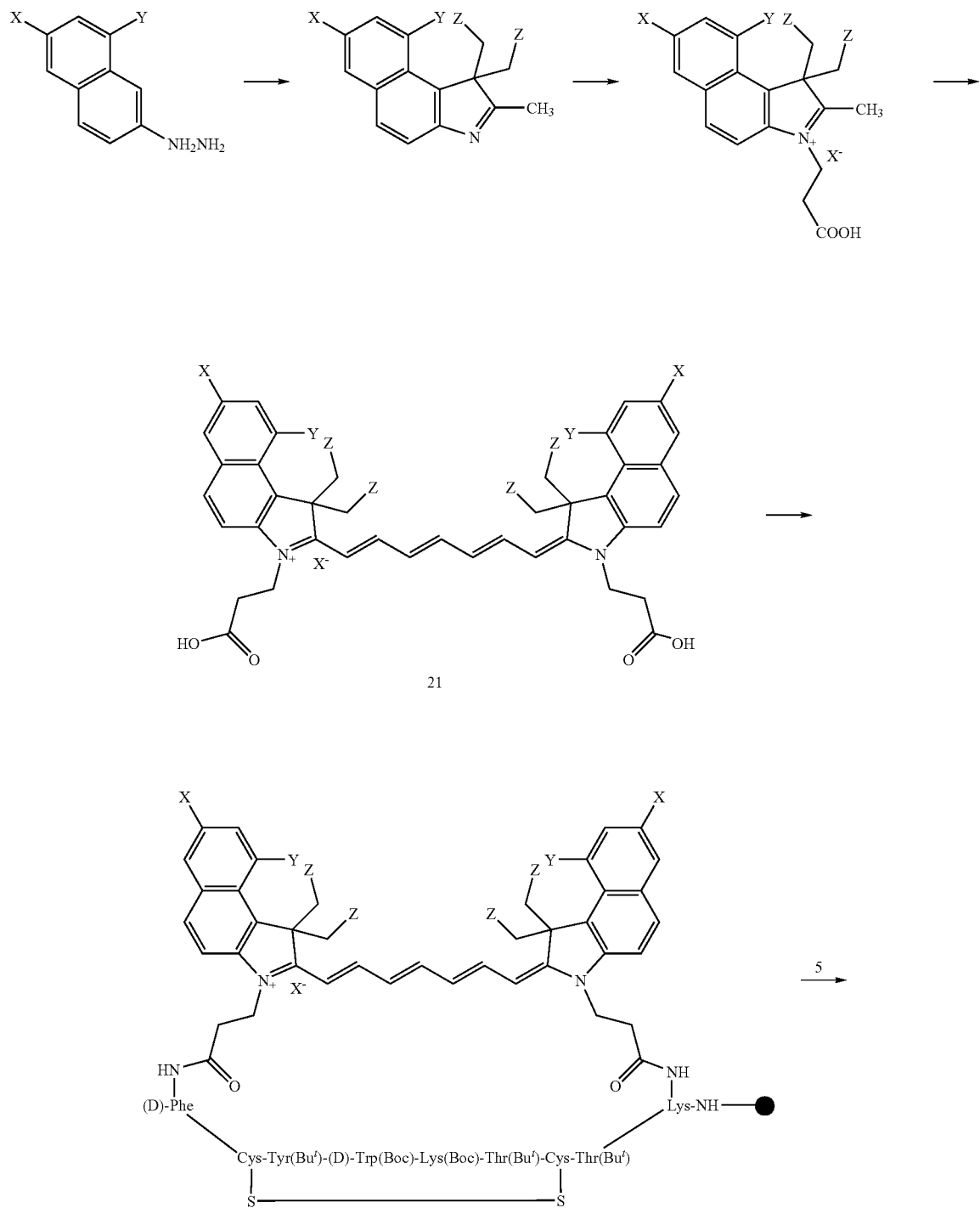

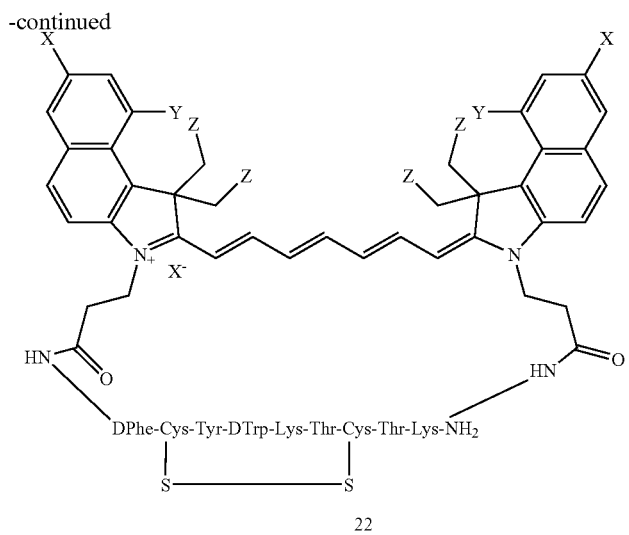
A similar method described in Example 2 and 13 was used to prepare the title compounds.
EXAMPLE 17
Synthesis of Rigid Cypate4 (23) and its Cyclic Octreotide Conjugate (24)
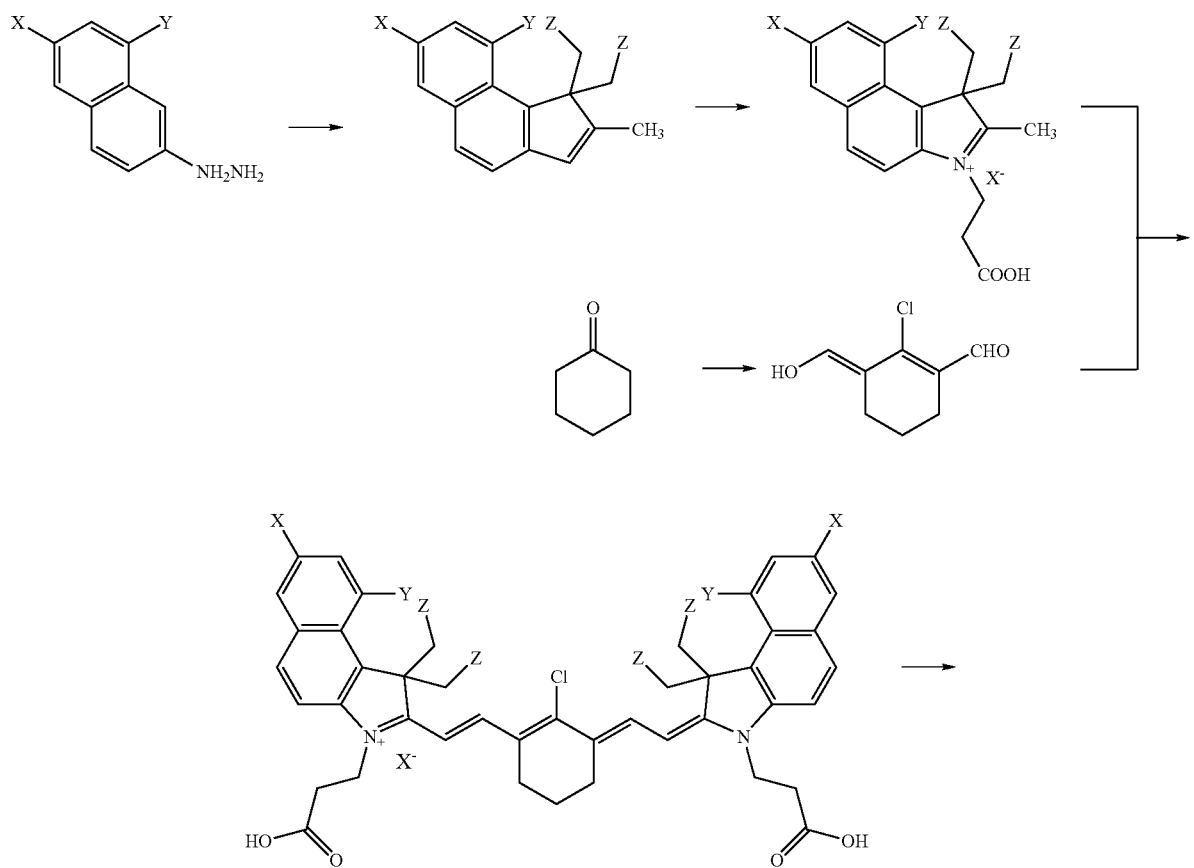

-continued
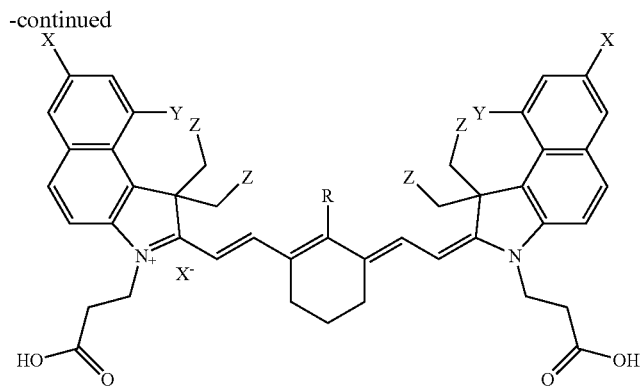
23
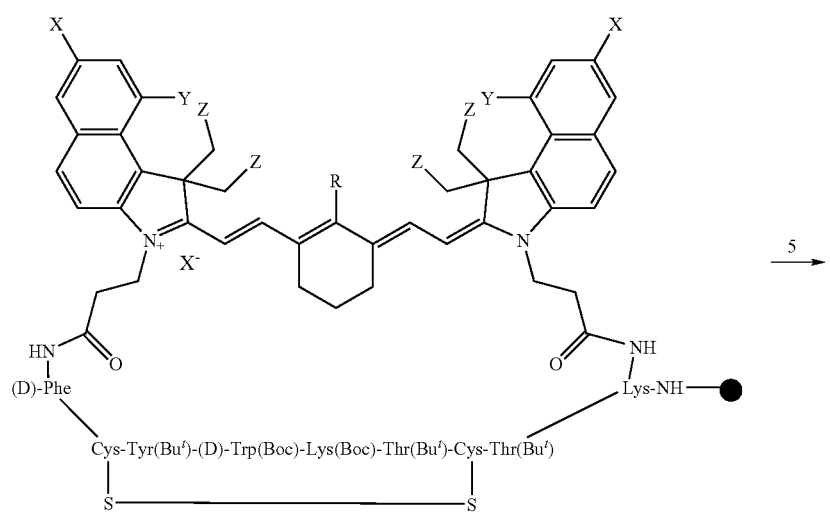
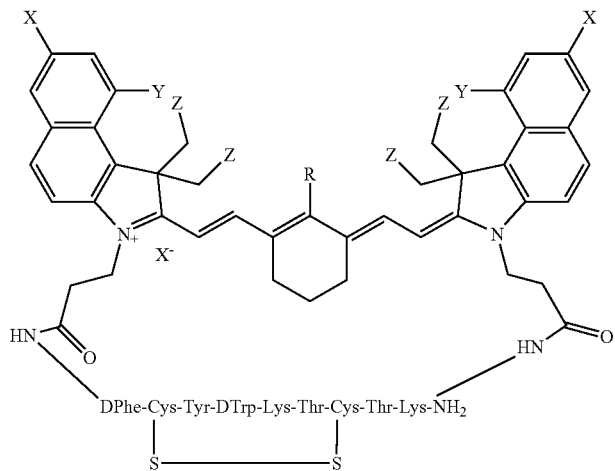
24
A similar method described in Example 2 and 13 was used to prepare the title compounds.

EXAMPLE 18
Synthesis of Rigid Cypate4 (25) and its Cyclic Octreotide Conjugate (26)
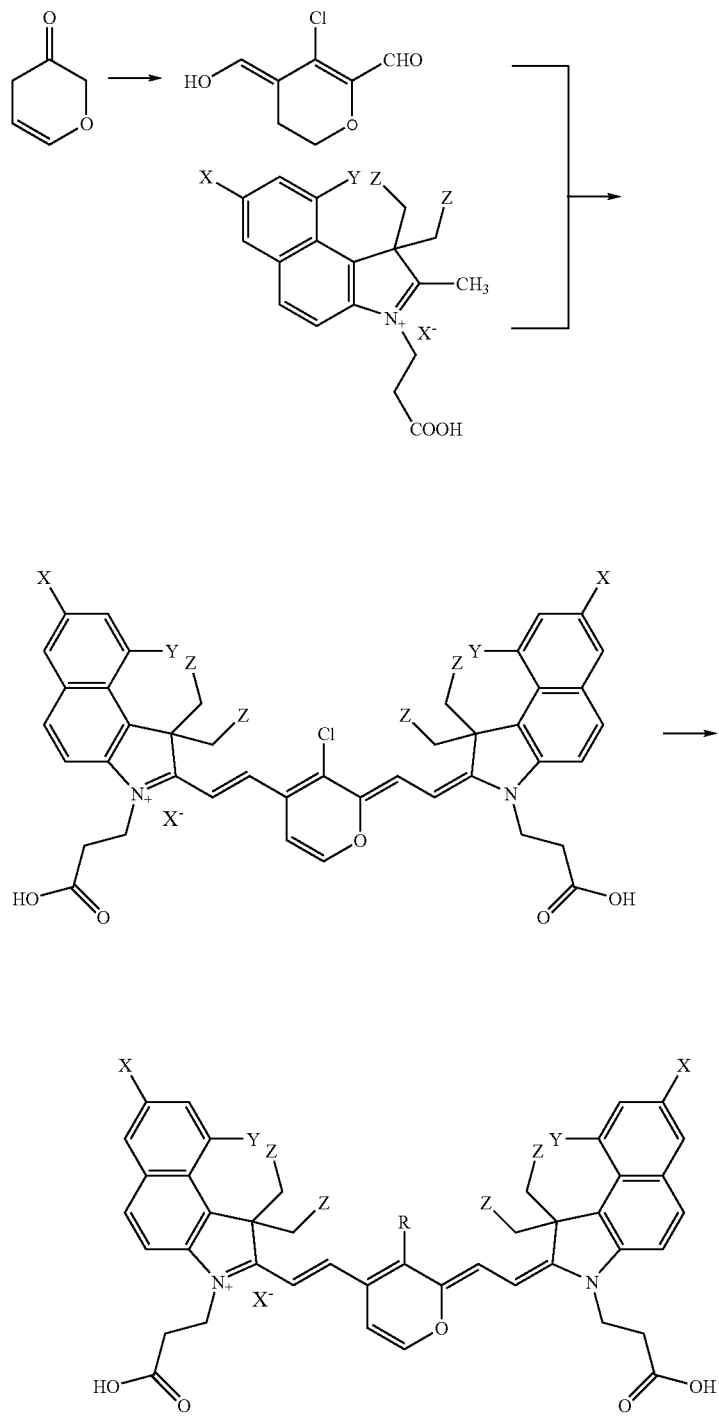
25

-continued
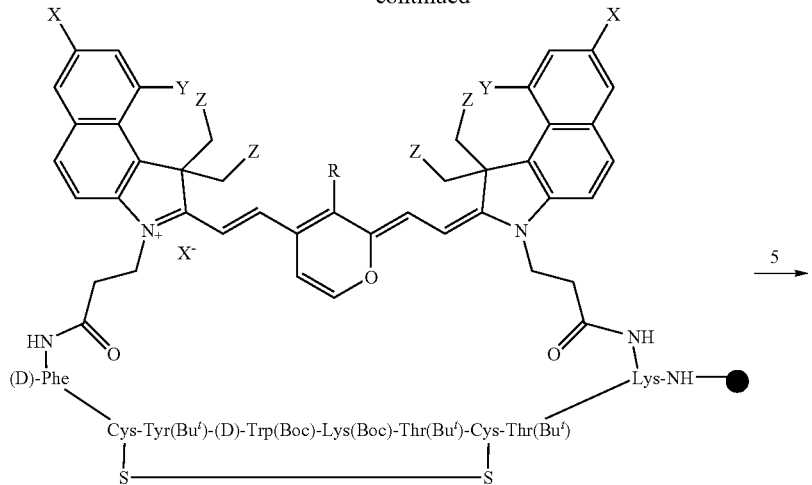
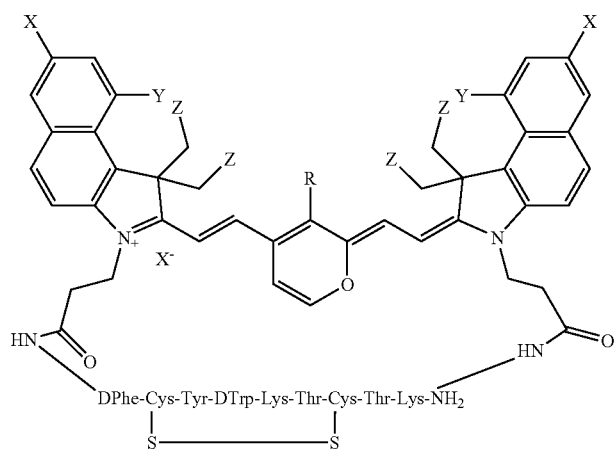
26
EXAMPLE 19
Synthesis of Cyclic Substituted Cypate4—RGD Peptide Conjugates (27)
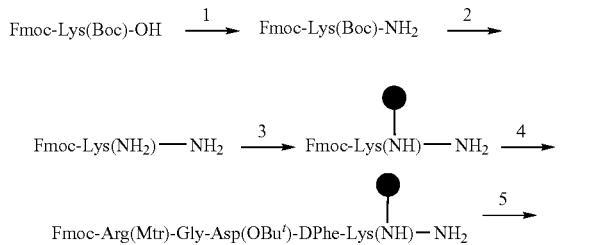
-continued
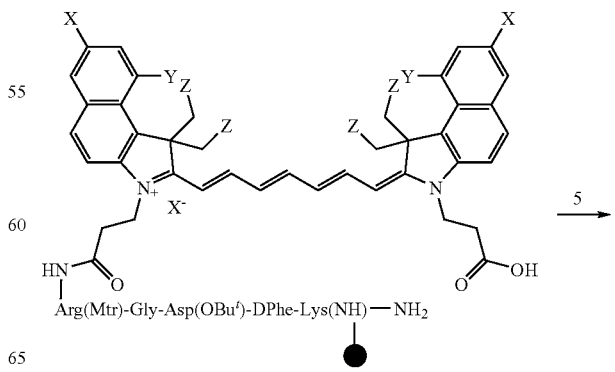

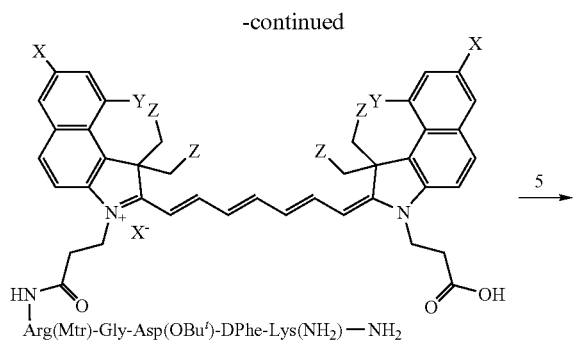

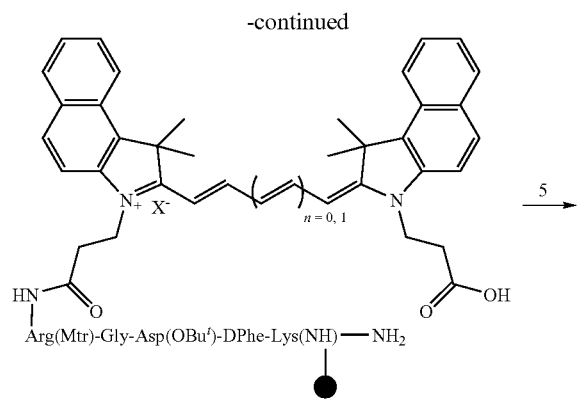

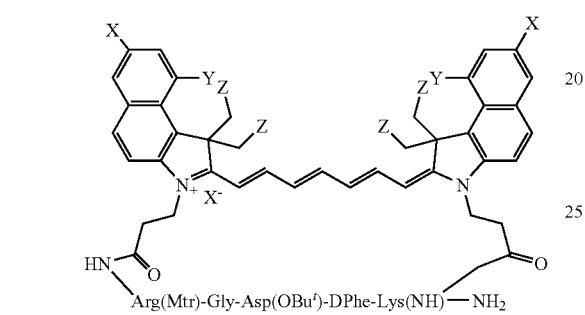

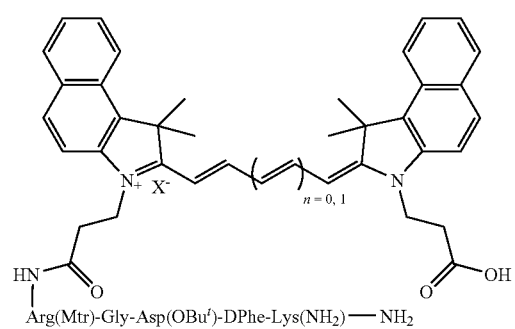

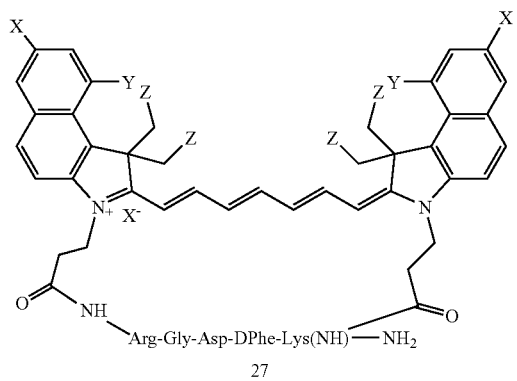

27

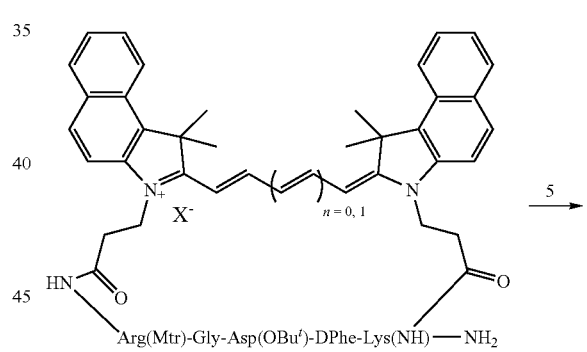

The RGD peptide analog was assembled on 2-chlorotrityl chloride resin by conventional Fmoc chemistry. The conjugation and cyclization were performed using the similar procedure described in Example 12 using substituted cypate4 in the place of Cypate4 and the protected RGD peptide instead of bombesin peptide.

EXAMPLE 20

Synthesis of Cyclic Cypate2- and Cypate3—RGD Peptide Conjugates (28)

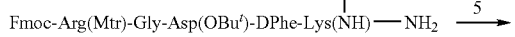

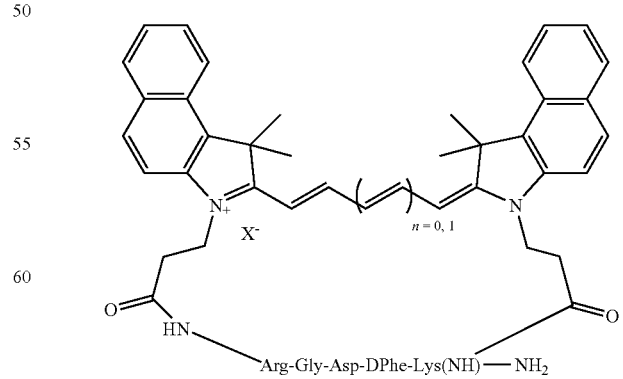

28

The title compounds were prepared using the similar procedure described in Example 12 using substituted cypate2 (8) and cypate3 (7) in the place of Cypate4 and the protected RGD peptide instead of bombesin peptide.

EXAMPLE 21

Conjugation of Rigid Cypate4 (23) with RGD Peptide Analog (29)

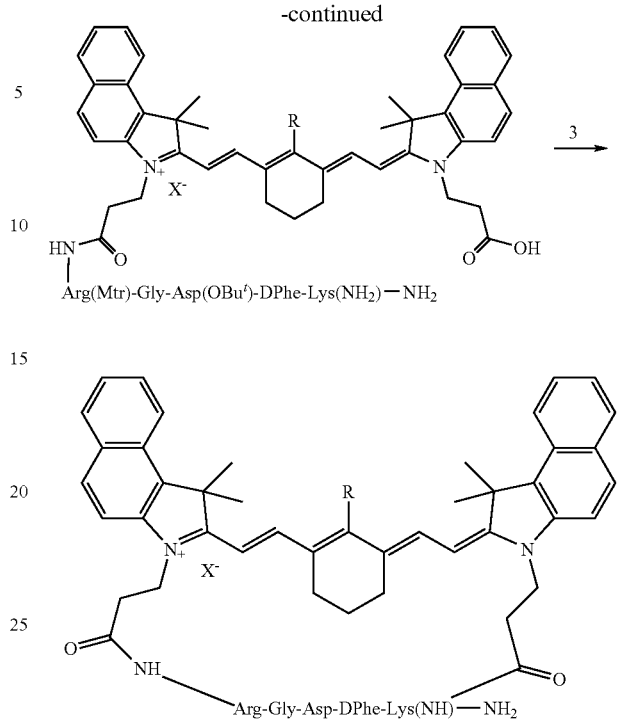

Arg(Mtr)-Gly-Asp(OBu$^t$)-DPhe-Lys(NH$_2$)—NH$_2$

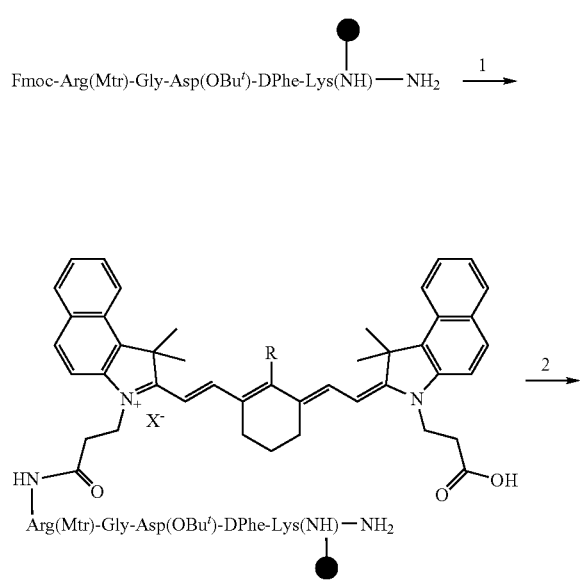

29

The title compounds were prepared using the similar procedure described in Example 17 using the protected RGD peptide instead of Octreotide peptide.

EXAMPLE 22

Conjugation of Rigid Cypate4 (25) with RGD Peptide Analog (30)

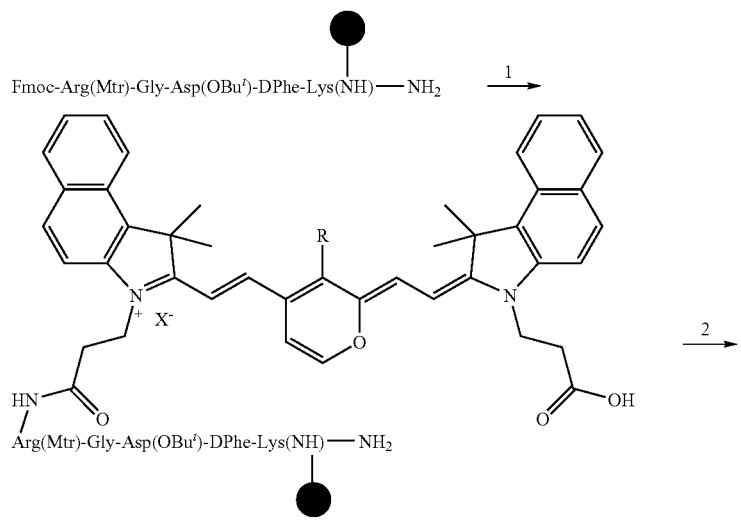

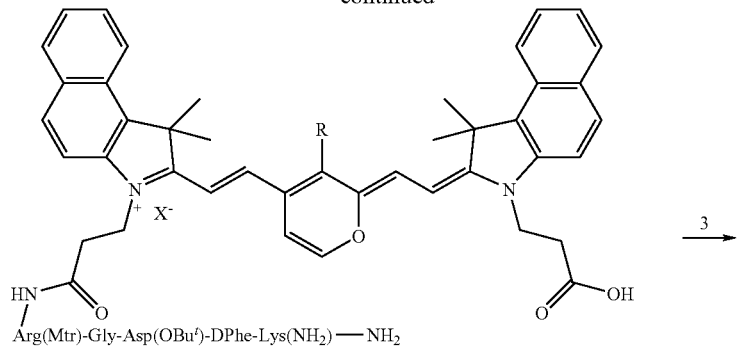
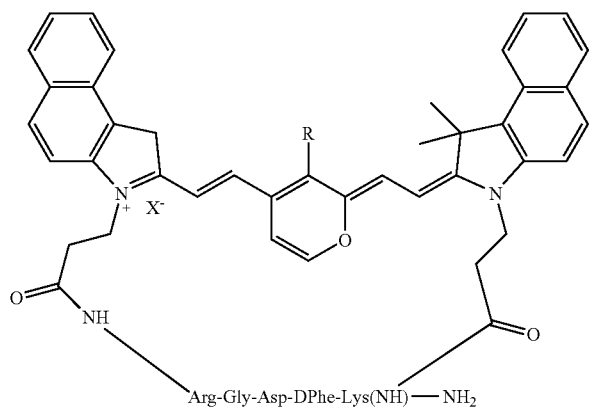
30
The title compounds were prepared using the similar procedure described in Example 18 using the protected RGD peptide in the place of Octreotide peptide.
EXAMPLE 23
Conjugation of Cypate4 Analog with RGD Peptide Analog (31)
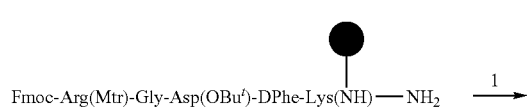
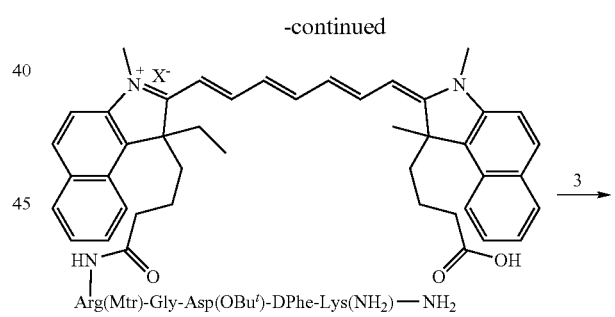
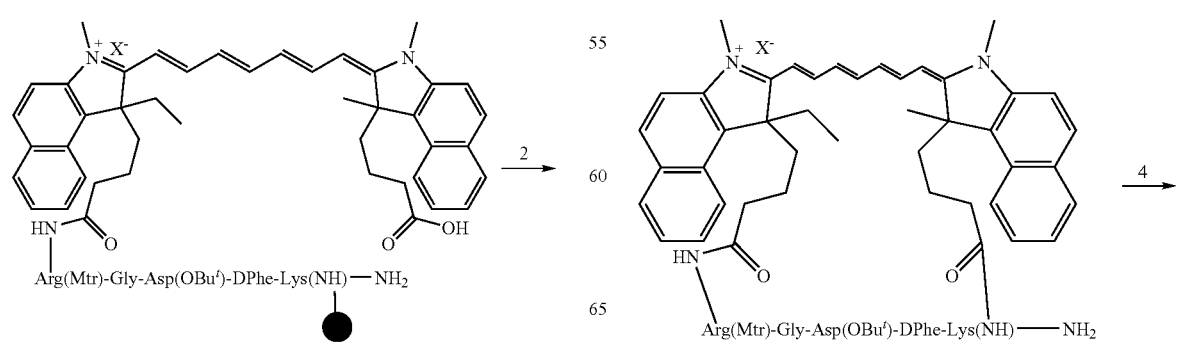

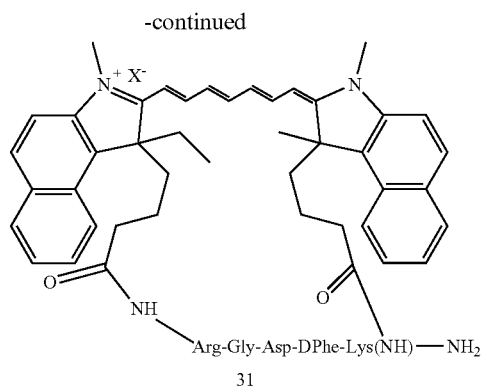
The title compound was prepared using the similar procedure described in Example 16.
EXAMPLE 24
Conjugation of Cypate4 Analog with RGD Peptide Analog (32)
The title compound was prepared using the similar procedure described in Example 23.
EXAMPLE 25
Conjugation of Cypate4 Analog with RGD Peptide Analog (33)
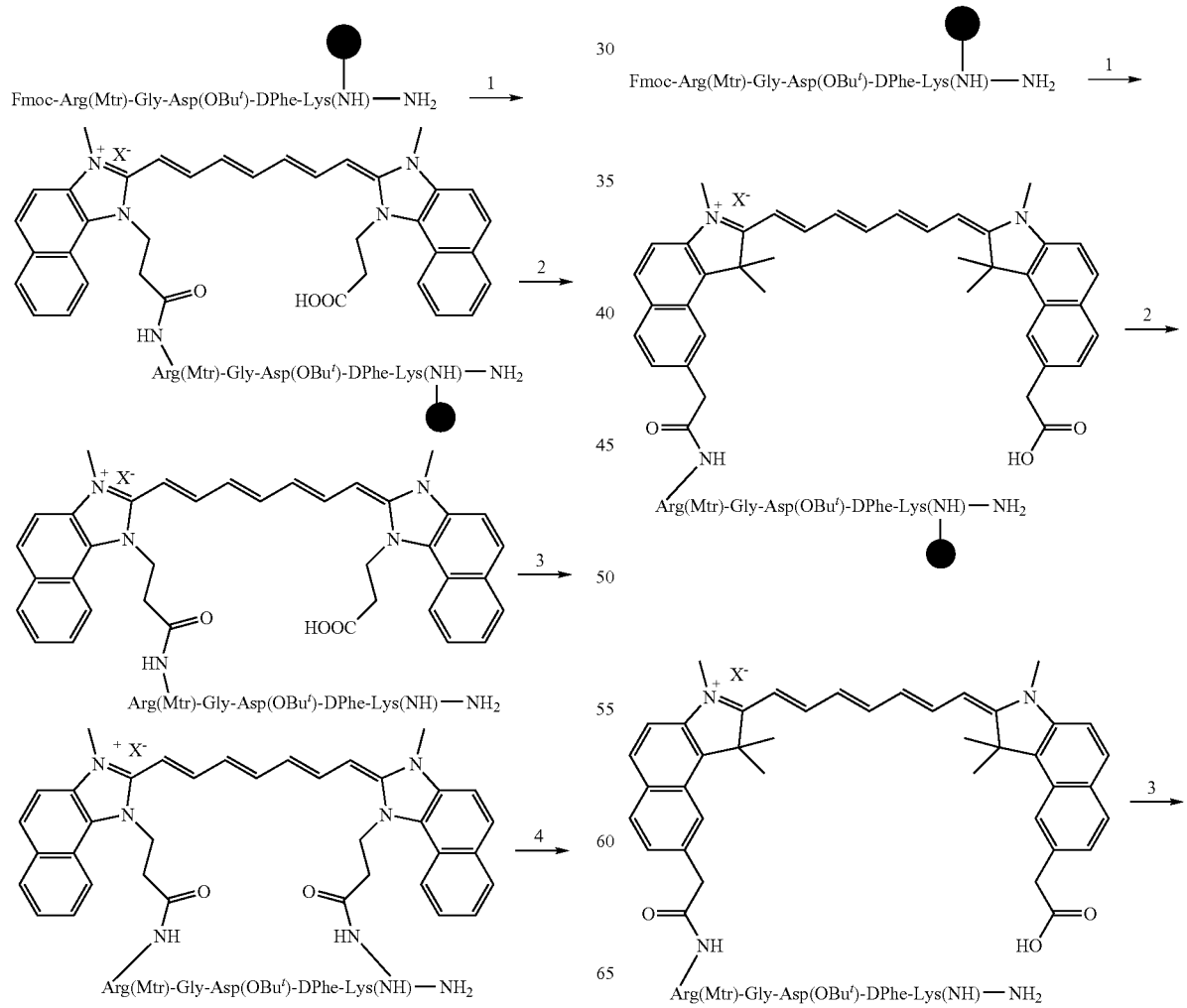

-continued

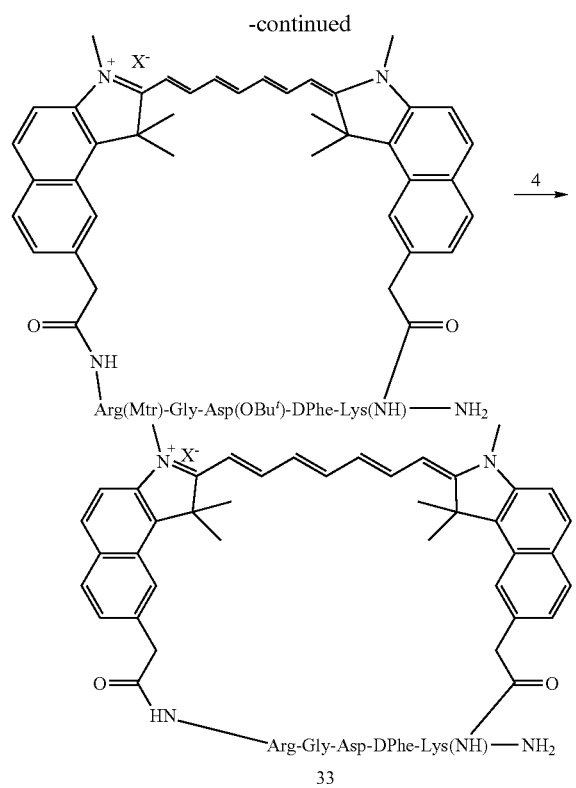

The title compound was prepared using the similar procedure described in Example 23.

EXAMPLE 25

Determination of Spectral Properties of Optical Probes

Figure 2A:
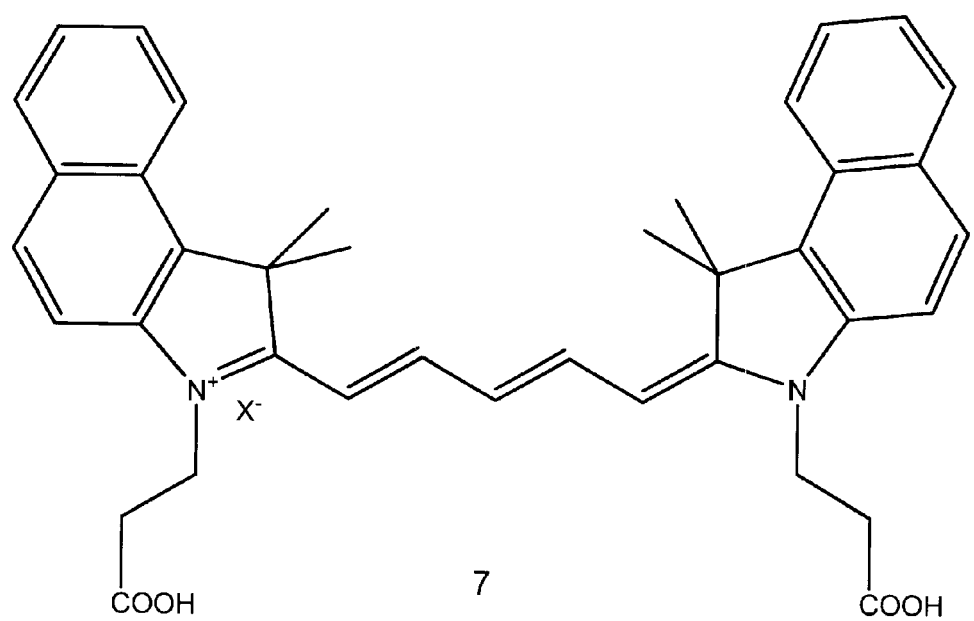
FIG. 2 depicts the (A) structure, (B) UV-Vis spectrum, and (C) emission spectrum of cypate3 (7).
Figure 2:
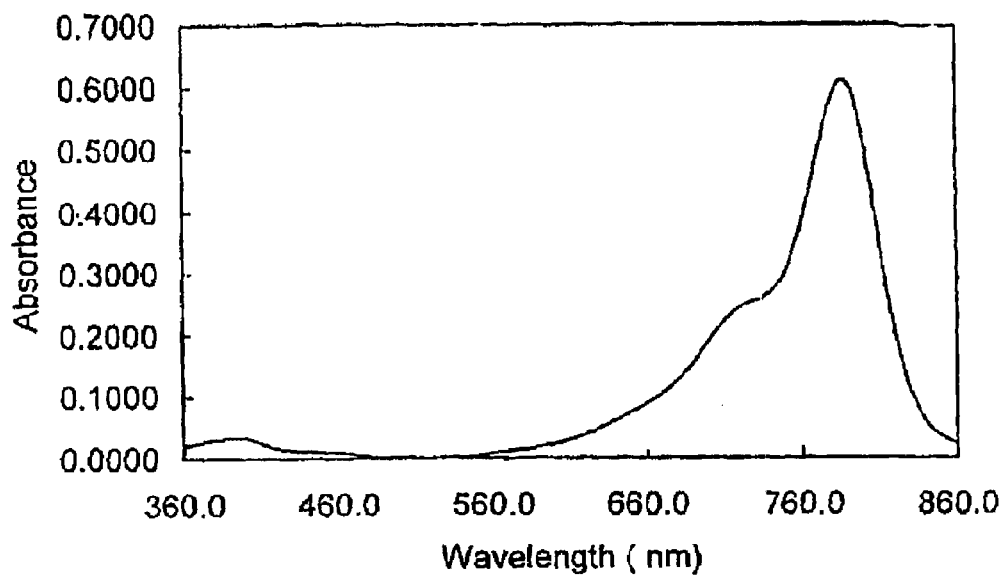
Figure 2:
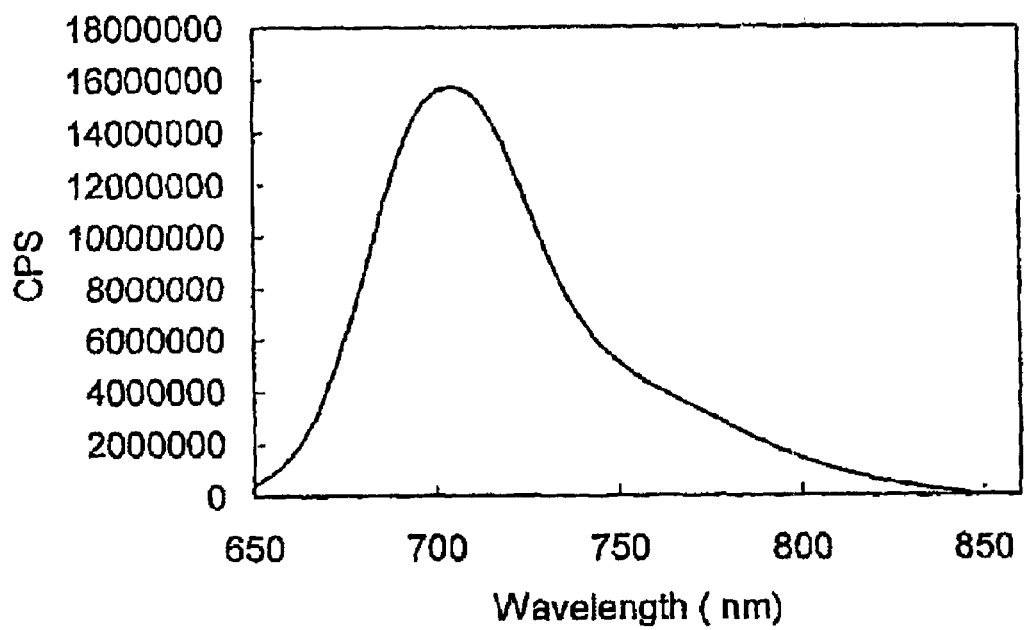
Figure 3A:
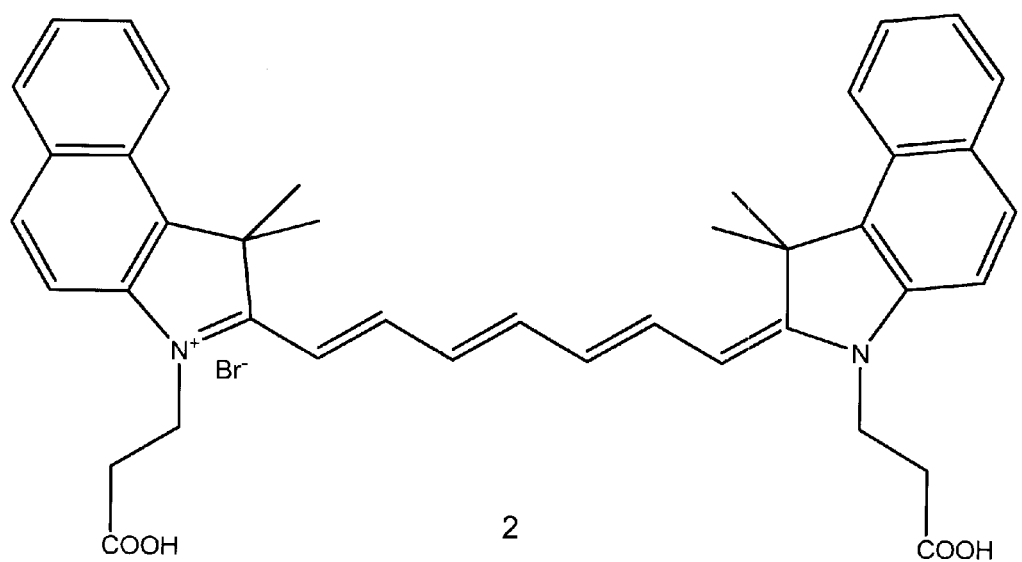
FIG. 3 depicts the (A) structure, (B) UV-Vis spectrum, and (C) emission spectrum of cypate4 (2).
Figure 3:
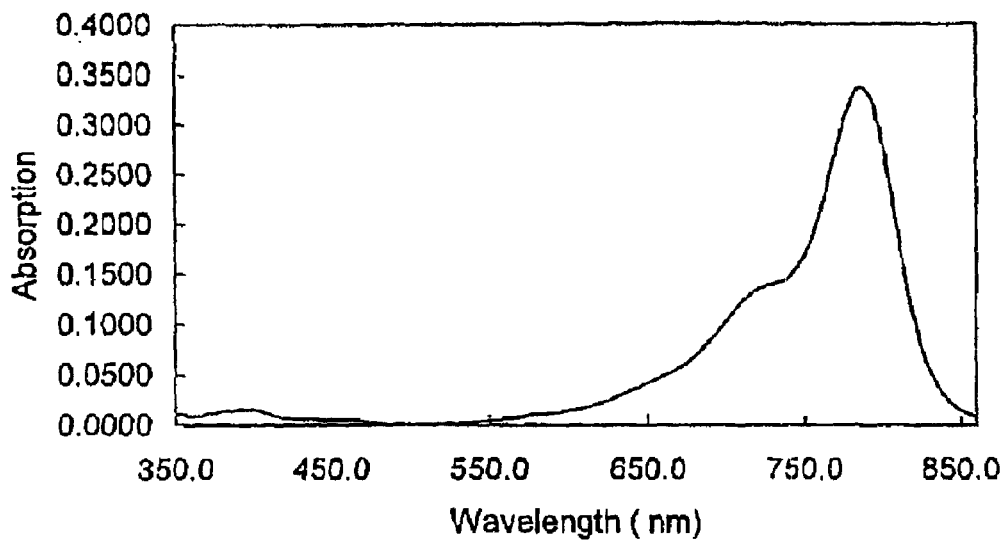
Figure 3:
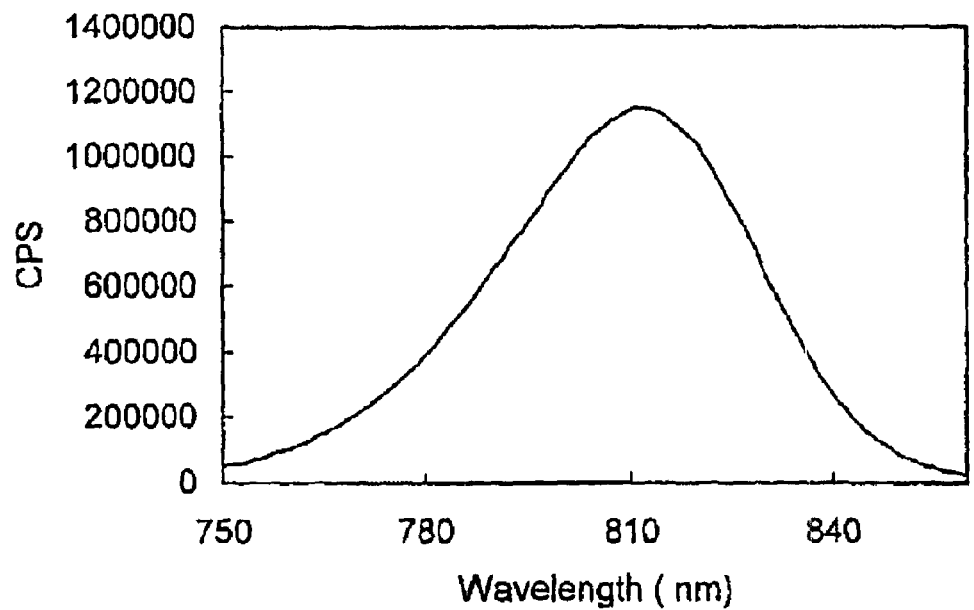
Figure 4A:
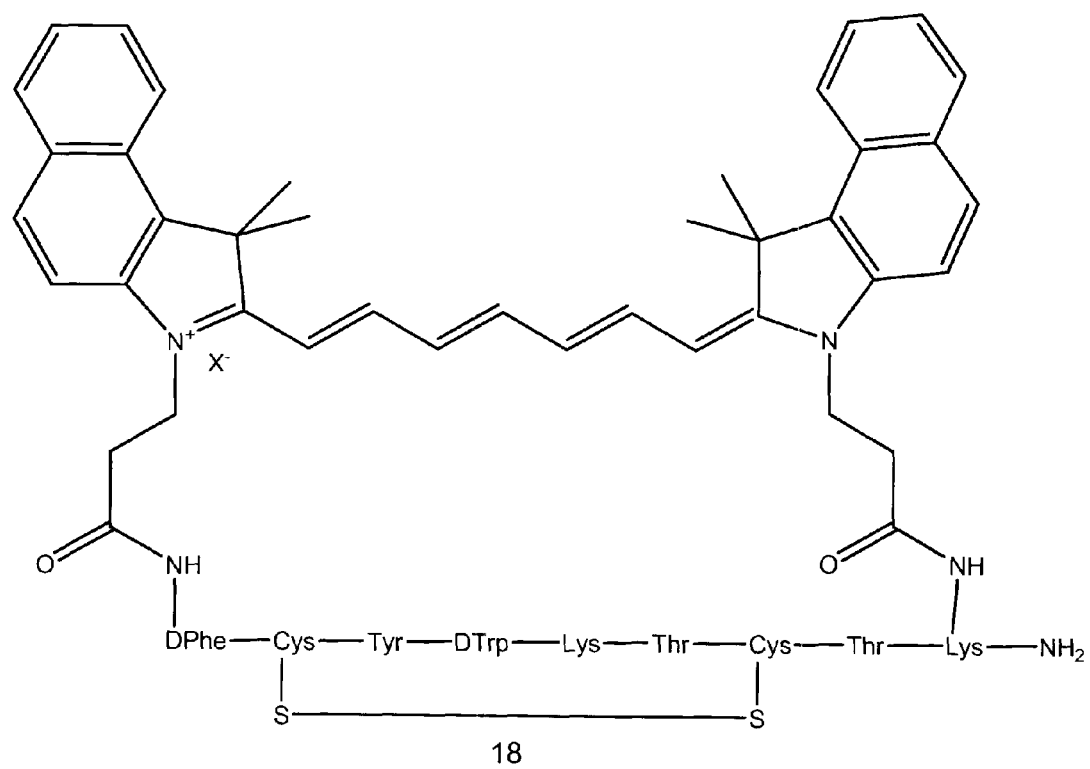
FIG. 4 depicts the (A) structure, (B) UV-Vis spectrum, and (C) emission spectrum of cyclo(cypate-octreotide) (18).
Figure 4:
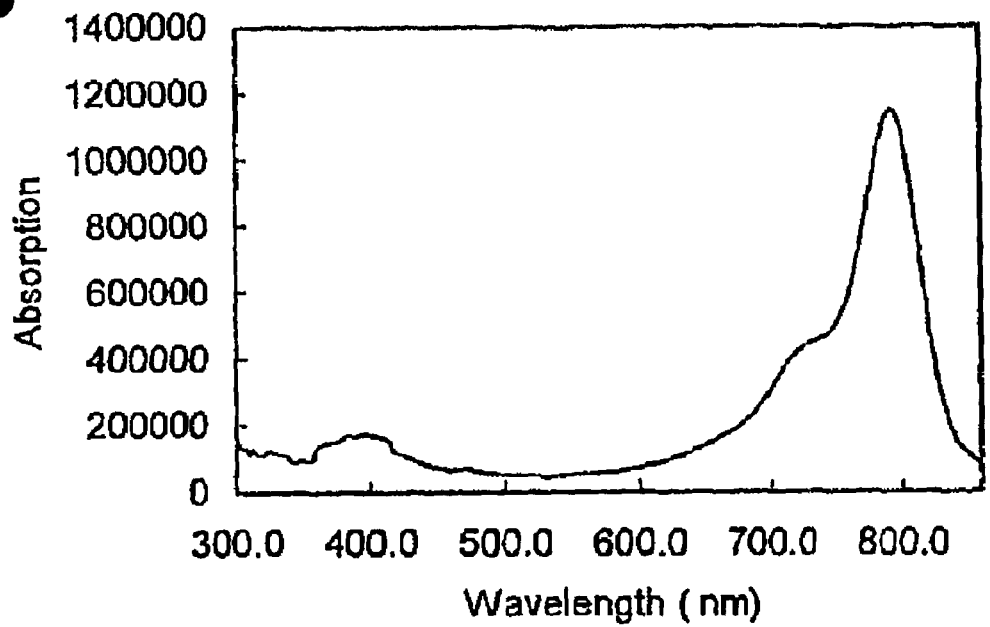
Figure 4:
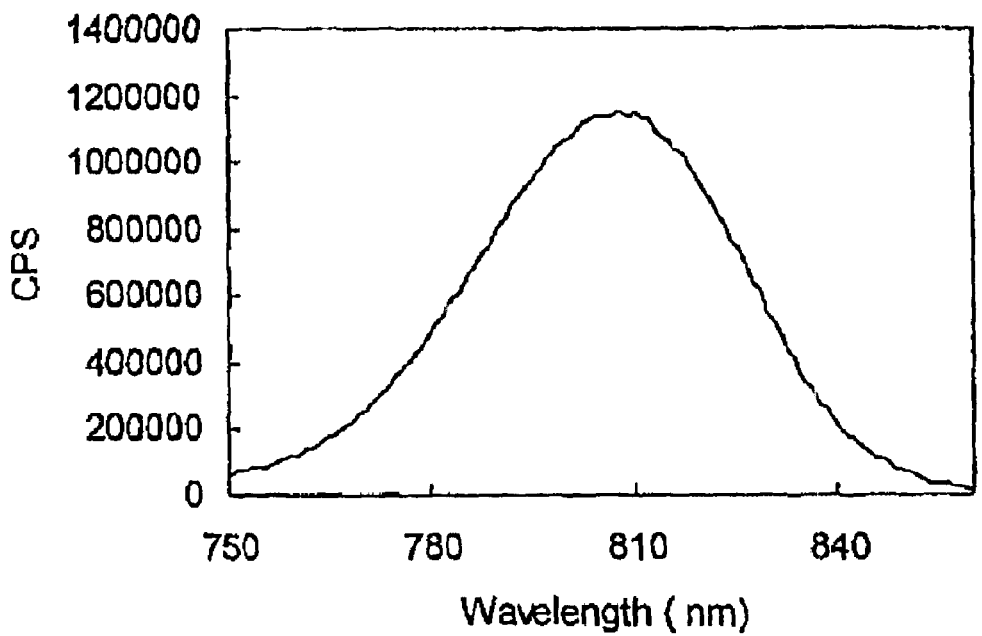
Figure 5:
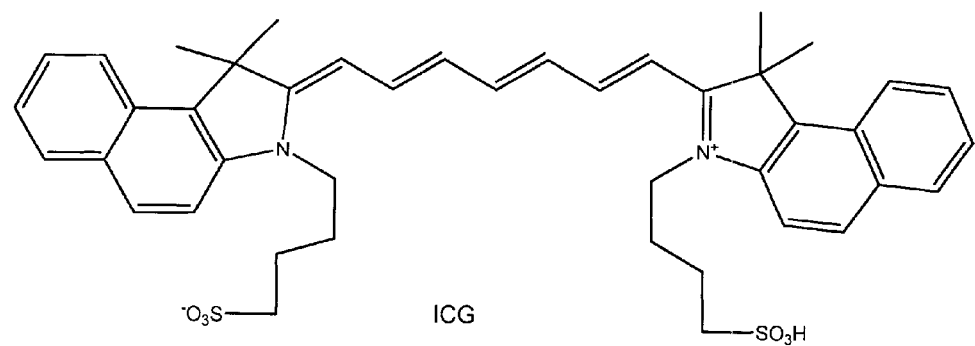
FIG. 5 depicts the (A) structure, (B) UV-Vis spectrum, and (C) emission spectrum of ICG.
Figure 5:
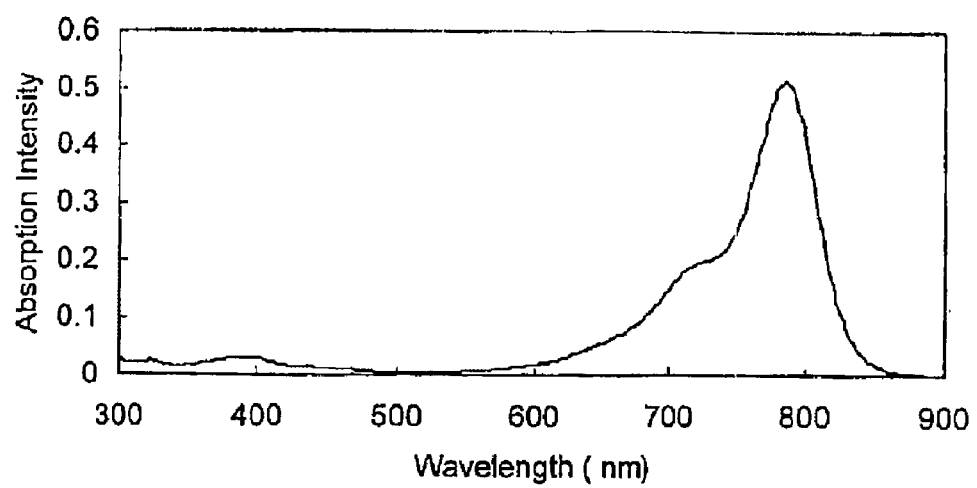
Figure 5C:
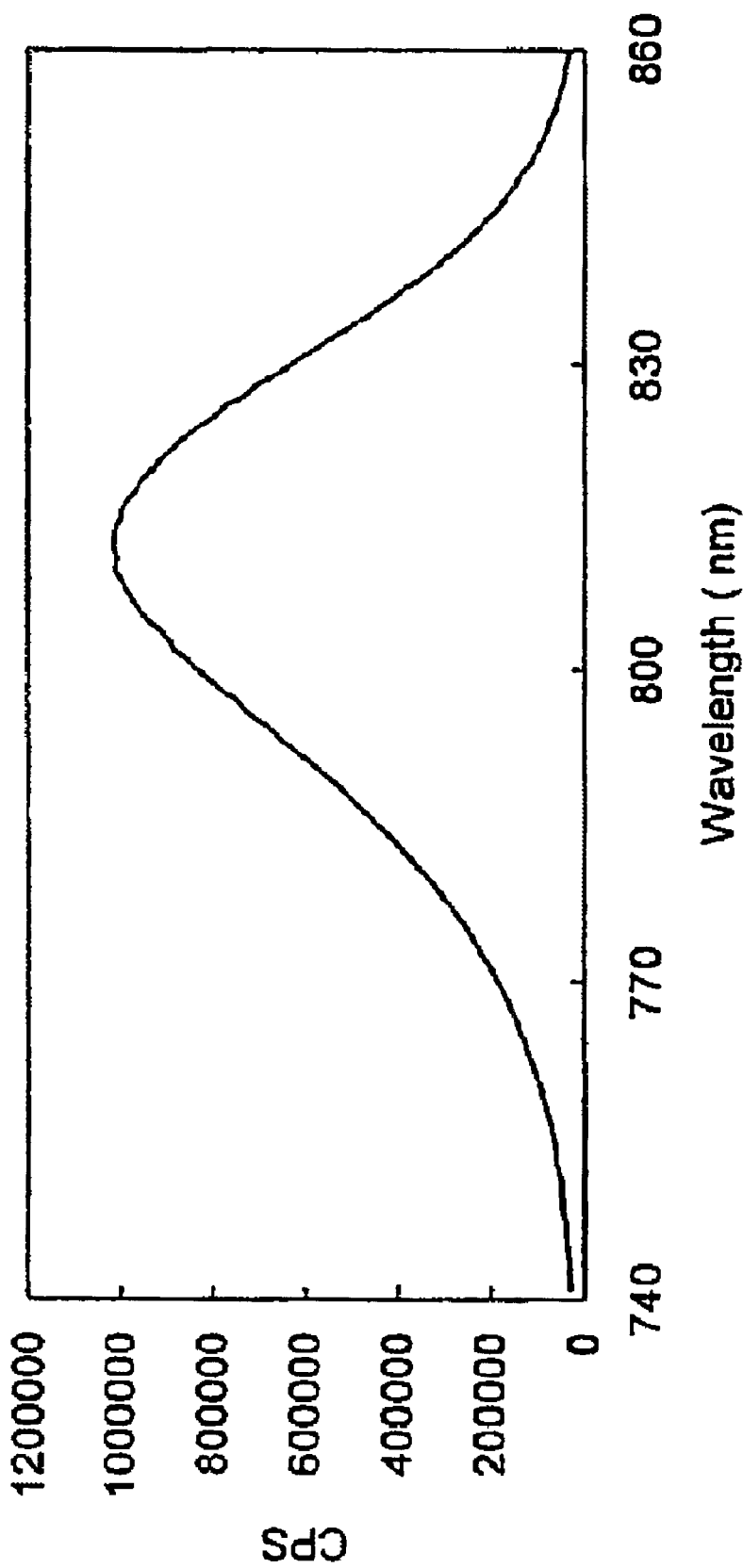
Figure 6A:
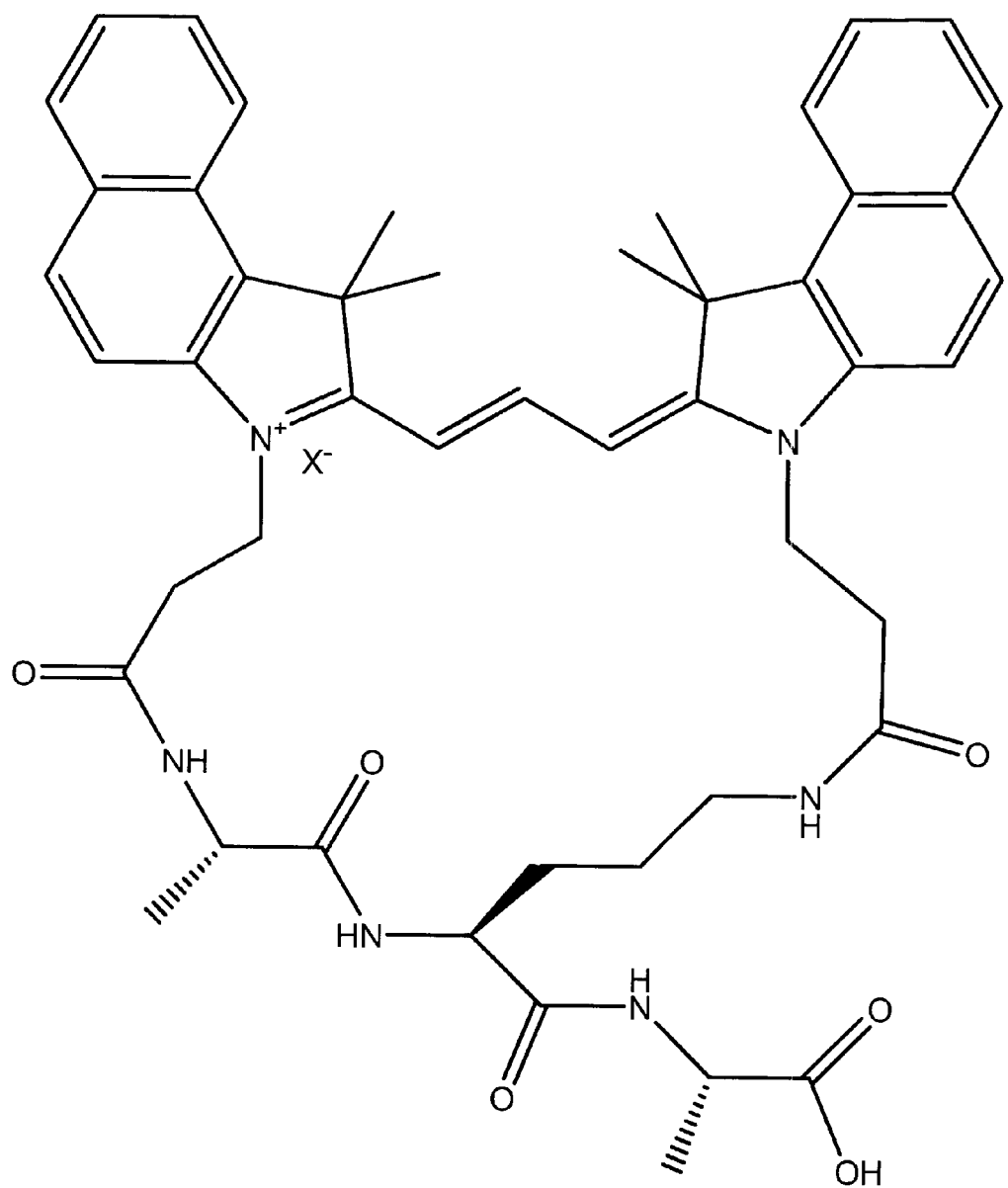
FIG. 6 depicts the (A) structure, (B) UV-Vis spectrum, and (C) emission spectrum of cyclo(cypate2-DPhe-Lys)-Thr-OH.
Figure 6:
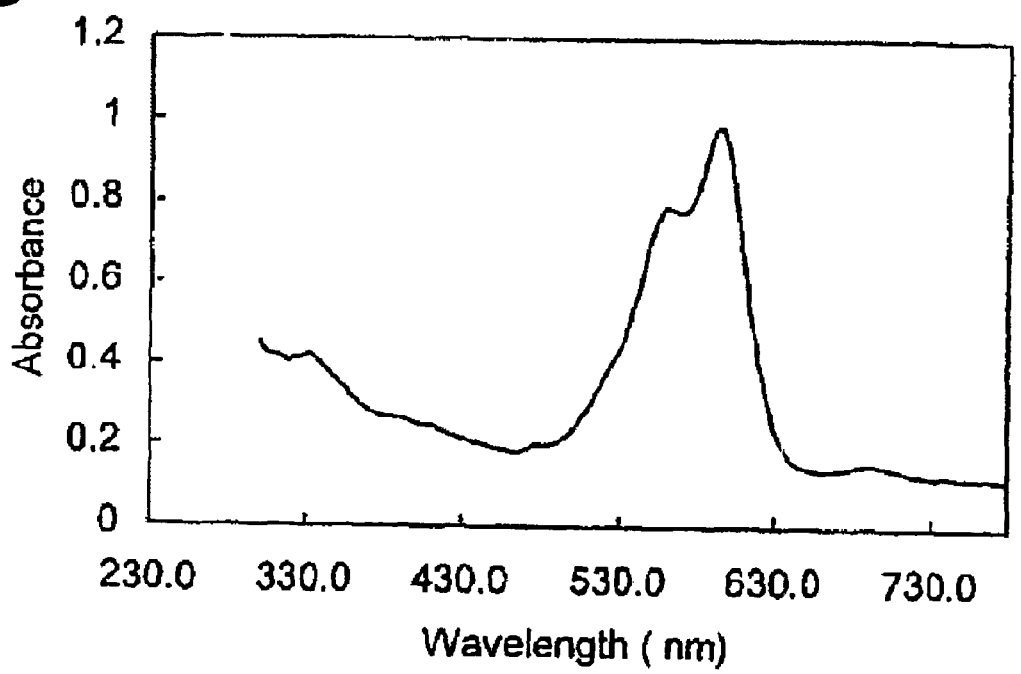
Figure 6:
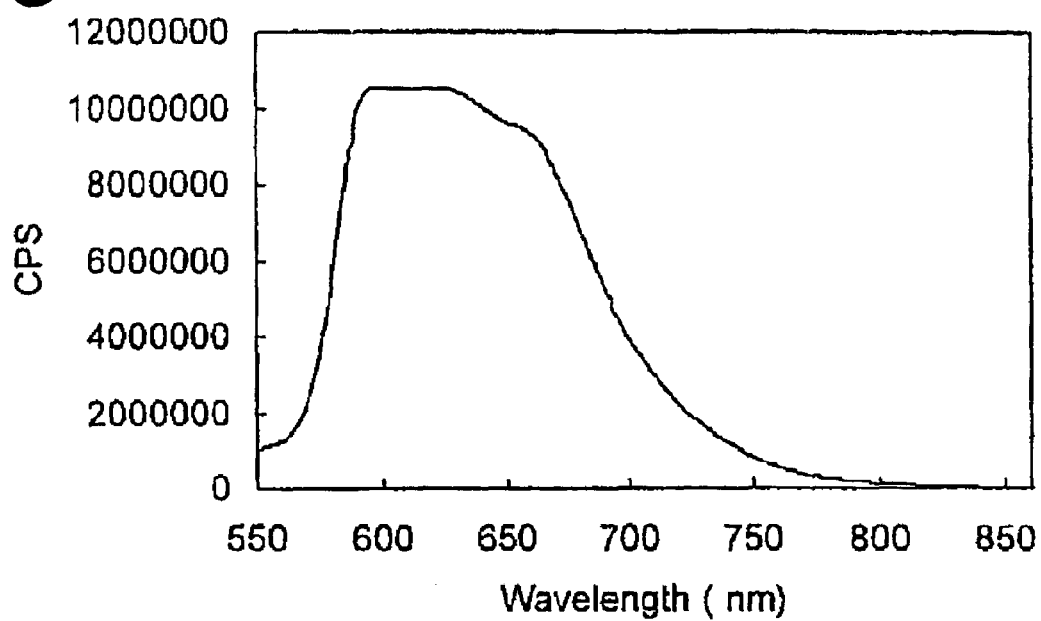
Figure 7A:
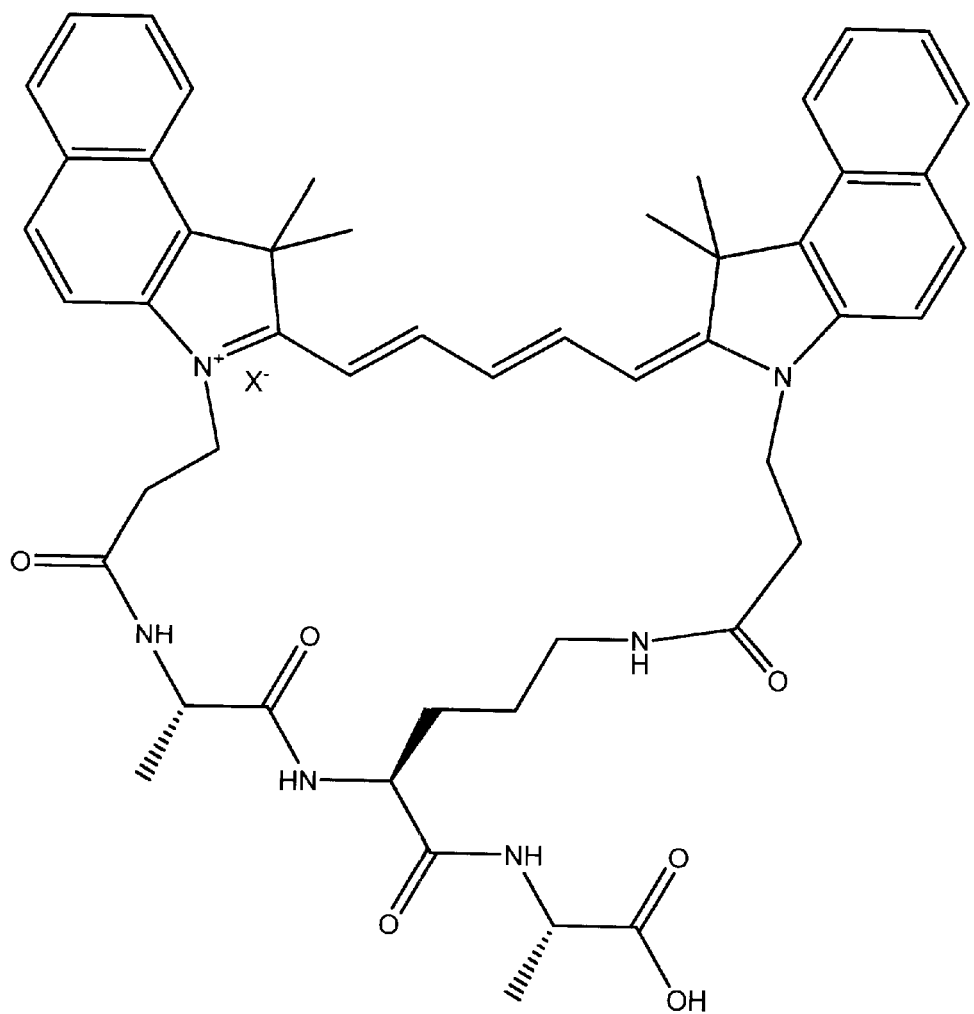
FIG. 7 depicts the (A) structure, (B) UV-Vis spectrum, and (C) emission spectrum of cyclo(cypate3-DPhe-Lys)-Thr-OH.
Figure 7:
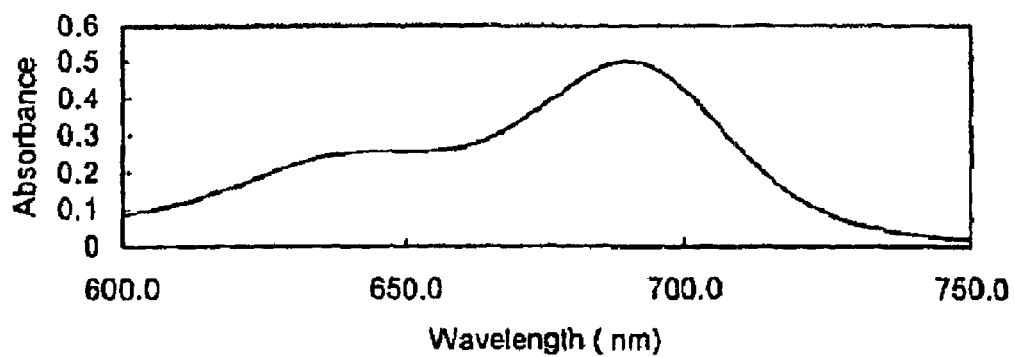
Figure 7:
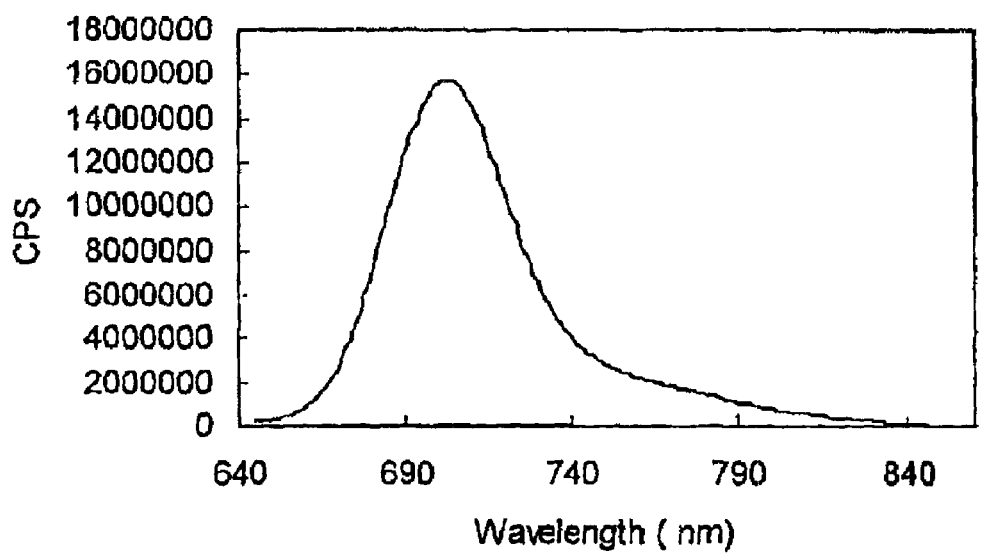

The absorption and emission spectral properties of representative optical probes prepared are shown in FIGS. 1-7. Stock solutions (1.0 mM) of the probes were prepared by dissolving in anhydrous DMSO (99.99%). The spectral measurements were obtained by sequentially adding 0.5about 2.0 µL aliquots of the stock solutions via a micropipette into 3 mL of 25% aqueous DMSO solution in a quartz cuvette and stirring for equilibration prior to acquiring the spectra.

EXAMPLE 26

Determination of Receptor Binding Affinity of Fluorescent Probes (Part A)

The binding affinity of somatostatin analogues was carried out using $^{111}$In-DTPA-octreotide in AR42J tumor cells according to previously reported methods with minor modifications (Lewis, J. S., Lewis, M. R., Srinivasan, A., Schmidt, M. A., Wang, J., and Anderson, C. J. (1999) Comparison of Four $^{64}$Cu-labeled Somatostatin Analogs in vitro and in a Tumor-bearing Rat Model: Evaluation of New Derivatives for PET Imaging and Targeted Radiotherapy. *J. Med. Chem.* 42, 1.341-1347). The AR42J rat pancreatic carcinoma cell line is known to express SSTR2 both in vitro and in vivo ((Rosewicz, S., Vogt, D., Harth, N., Grund, C., Franke, W. W., Ruppert, S., Schweitzer, E., Riecken, E.-O., and Wiedenman, B. (1992) An Amphicrine Pancreatic Cell Line: AR42J Cells Combine Exocrine and Neuroendocrine Properties. *Eur. J. Cell Biol.* 59, 80-91; Christophe, J. (1994) Pancreatic Tumoral Cell Line AR42J: An Amphicrine Model. *Am. J. Physiol.* (*Gastrointest. Liver Physiol.*) 266 (29), G963-G971). A preparation of cell membranes was made from AR42J cells by brief sonication in ice-cold 50 mM Tris buffer containing 1.0 mM EGTA, 0.5 mM PMSF 0.01 mg/ml, leupeptin, 0.2 mg/ml bacitracin, 0.01 mg/ml pepstatin. The suspension was centrifuged at 13,000 rpm and 4° c. for 10 min. and the pelleted membranes were re-suspended in ice-cold 50 mM Tris buffer. Assays were performed using Millipore FC96 plates and the Millipore Multiscreen system (Bedford, Mass.) (1). Triplicates of 50 µl membranes (60 µg/well) were incubated with 50 µl radioligand (30-40,000 cpm) and increasing concentration cold competitors in binding buffer (50 mM Tris-CHl, 5 mM $MgCl_2$, 0.1 mg/ml BSA) in a total volume of 250 µl per well at 37° C. for 2 h. Following incubation, membranes were filtered on a vacuum manifold and washed twice with binding buffer. The filters containing membrane-bound radioactivity were removed from the assay plate and counted using a Beckman 8000 automated well-typed counter (Fullerton, Calif.). Specific binding was calculated by subtracting the non-specifically bound radioactivity from that of total binding. The best-fit $IC_{50}$ values were calculated using PRISM™ (Graphpad, San Diego, Calif.). Radiolabeling of DTPA-octreotide with $^{111}$In was carried out in 0.1 M NaOAc (pH 6.5, room temperature, 30 min incubation) specific activity of and radiochemical purity was confirmed greater than 98% by radio TLC. The specific activity of $^{111}$In-DTPA-octreotide ranged from 1200 Ci/mmol to 1500 Ci/mmol.

Analysis of the receptor binding assay of a representative somatostatin-avid macrocyclic molecule (compound 18) shows that it has an $IC_{50}$ value of 8.17 nM relative to $^{111}$In-DTPA-octreotide, demonstrating that the peptide's receptor binding affinity was retained in the nanomolar range.

|  | Experimental | |
| --- | --- | --- |
| Competing Ligand | IC50 (nM) | 95% CI (nM) |
| Compound 18 | 8.170 | 4.94-13.52 |

Contrast Agent-mediated Optical Imaging of Tumors (Part B)

The instrument consists of an excitation source and a charge-coupled device (CCD) camera for signal detection. To image compounds such as compound 18 that absorb and emit radiation in the near infrared region, a nominal 780 nm collimated solid state laser source was used to excite the compounds. The nominal 50 mW of incident power from the laser was reduced to about 20 mW at the output of the fiber optic bundle. A CCD camera (12 bit, 1024×1024 pixel, back illuminated) was equipped with the appropriate interference filter to capture the emitted photons at 830 nm. Biodistribution of the dyes and receptor-specific optical contrast agent in mice were performed by injecting 0.5 mL of a 1 µM solution of the compound via the lateral tail vein of tumor (CA20948) bearing mice. The precursor compound to macrocyclization (compound 2) clears from the blood within 1 h postinjection and accumulates in the liver. In contrast, injection of somatostatin-avid optical probes in CA20948 tumor-bearing mice preferentially accumulates in the tumor.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Becker A, Licha K, Kress M and Riefke B (1999). "Transferrin Mediated Tumor Delivery of Contrast Media for Optical Imaging and Magnetic ResonanceImaging", Biomedical Optics meeting, Jan. 23-29, 1999, San Jose, Calif.

Brinkley M (1993). "A Brief Survey of Methods for Preparing Protein Conjugates with Dyes, Haptens, and Cross-Linking Reagents", Perspectives in Bioconjugate Chemistry (Ed. Claude Meares, ACS Publication, Washington, D.C.), pp. 59-70.

de Jong M, et al. (1998). Cancer Res. 58:437-441.

Jain R K (1994). "Barriers to Drug Delivery in Solid Tumors", Scientific American 271:58-65.

Patonay G and Antoine M D (1991). "Near-Infrared Fluorogenic Labels: New Approach to an Old Problem", Analytical Chemistry, 63:321A-327A and references therein.

Slavik J (1994). Fluorescent Probes in Cellular and Molecular Biology (CRC Press, Inc.).

Patents and Published Patent Applications Lee L G and Woo S L. "N-Heteroaromatic ion and iminium ion substituted cyanine dyes for use as fluorescence labels", U.S. Pat. No. 5,453,505.

Hohenschuh E, et al. "Light imaging contrast agents", WO 98/48846.

Turner J, et al. "Optical diagnostic agents for diagnosis of neurodegenerative diseases by means of near infrared radiation (NIR radiation)", WO 98/22146.

Licha K, et al. "in vivo diagnostic process by near infrared radiation", WO 96/17628.

Snow R A, et al., "Compounds", WO 98/48838.

What is claimed is:

1. A macrocyclic bioconjugate imaging agent comprising Formula 14:

Formula 14

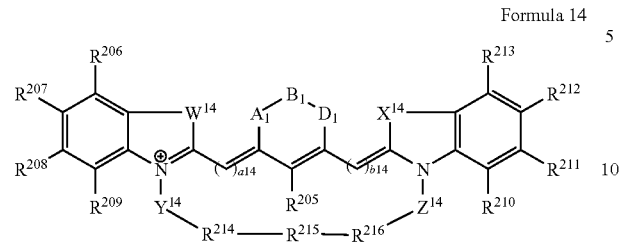

wherein:
a14 and b14 are integers from 0 to 7;
$W^{14}$ and $X^{14}$ are independently selected from the group consisting of —$CR_aR_b$—, —O—, —$NR_b$—, —S—, and —Se—; wherein $R_a$ and $R_b$ are independently selected from the group consisting of hydrogen, C1-C20 alkyl, C1-C14 aryl, C1-C20 alkoxyl, C1-C20 polyalkoxyalkyl, C1-C20 thioalkyl, C1-C20 carboxyl, C1-C20 aminoalkyl, C1-C20 hydroxyalkyl, C5-C20 polyhydroxyaryl, carbocyclic, heterocyclic, sulfonate, sulfate, thiol, sulfide, thioether, phosphonate, phosphate, phosphite, carboxylate, amino aryl, cyano, nitro, halogen, saccharide, peptide, protein, cell, glycopeptide, glycomimetic, peptidomimetic, antibody, antibody fragment, drug, hormone, metal chelating group, radioactive metal complex, non-radioactive metal complex, echogenic agent, arylpolysulfonate, fused aryl, and radioisotope;
$Y^{14}$ and $Z^{14}$ are independently selected from the group consisting of —$CR_a$—, C1-10 alkyl, C1-10 aryl, C1-10 alkoxyl, C1-20 polyalkoxyalkyl, C1-10 thioalkyl, C1-10 carboxylic acid, C1-10 aminoalkyl, C1-10 hydroxyalkyl, C5-C20 polyhydroxyaryl, —$(CH_2)_a$—$NR_a$—, —$CH_2(CH_2$—O—$CH_2)_b$—$CH_2$—O—, —$(CH_2)_a$—$CO_2$—, —$CH_2$—$(CH_2$—O—$CH_2)_b$—$CH_2$—$CO_2$—, —$CH_2$—$(CH_2$—O—$CH_2)_b$—$CH_2$—$NR_a$—, —$(CH_2)_a$—$N(R_b)$—$(CH_2)_c$—$CO_2R_e$—, —$(CH_2)_a$—$N(R_b)$—$CH_2$—$(CH_2$—O—$CH_2)_b$—$CH_2$—$CO_2R_e$—, —$(CH_2)_a$—$CONR_b$-Bm-, —$CH_2$—$(CH_2$—O—$CH_2)_b$—$CH_2$—$CONR_b$Bm-, —$(CH_2)_a$—$NR_b$CO-Bm-, —$CH_2$—$(CH_2$—O—$CH_2)_b$—$CH_2NR_b$CO-Bm-, —$(CH_2)_a$—$N(R_b)$—$(CH_2)_c$—$CONR_b$-Bm-, —$(CH_2)_a$—$N(R_b)$—$CH_2$—$(CH_2$—O—$CH_2)_b$—$CH_2$—$CONR_b$-Bm-, —$(CH_2)_aSO_3$—, —$(CH_2)_aS(O)$—, —$(CH_2)_aS$—, —$(CH_2)_aOSO_3$—, —$(CH_2)_aNR_bSO_3$——$(CH_2)_aCO_2(CH_2)_bSO_3$—$(CH_2)_aSO_3$—, —$(CH_2)_aOCO(CH_2)_cSO_3$—, —$(CH_2)_aCONR_b(CH_2)_cSO_3$—, —$(CH_2)_aNR_bCO(CH_2)_cSO_3$—, —$(CH_2)_aNR_bCONR_c(CH_2)_cSO_3$—, —$(CH_2)_aNR_bCSNR_c(CH_2)_cSO_3$—, —$(CH_2)_aO$-$CONR_e(CH_2)_cSO_3$—, —$(CH_2)_aPO_3R_e$—, —$(CH_2)_aOPO_3R_e$—, —$(CH_2)_aNR_bPO_3R_e$—, —$(CH_2)_aCO_2(CH_2)_cPO_3R_e$—, —$(CH_2)_aOCO(CH_2)_bPO_3R_e$—, —$(CH_2)_aCONR_b(CH_2)_cPO_3R_e$—, —$(CH_2)_aNR_bCO(CH_2)_cPO_3R_e$—, —$(CH_2)_aNR_bCONR_c(CH_2)_bPO_3R_e$—, —$(CH_2)_aNR_bCSNH(CH_2)_cPO_3R_e$—, —$(CH_2)_aOCONR_b(CH_2)_cPO_3R_e$—, cyano, nitro, halogen, saccharide, peptide, protein, cell, glycopeptide, peptidomimetic, drug, hormone, metal chelating agent, radioactive metal complex, non-radioactive metal complex, echogenic agent, and arylpolysulfonate; wherein the subscripts a and c independently vary from 1 to 20, and b varies from 1 to 100; wherein $R_a$, $R_b$, and $R_c$, are independently selected from the group consisting of hydrogen, C1-C20 alkyl, C1-C14 aryl, C1-C20 alkoxyl, C1-C20 polyalkoxyalkyl, C1-C20 thioalkyl, C1-C20 carboxyl, C1-C20 aminoalkyl, C1-C20 hydroxyalkyl, C5-C20 polyhydroxyaryl, carbocyclic, heterocyclic, sulfonate, sulfate, thiol, sulfide, thioether, phosphonate, phosphate, phosphite, carboxylate, amino aryl, cyano, nitro, halogen, saccharide, peptide, protein, cell, glycopeptide, glycomimetic, peptidomimetic, antibody, antibody fragment, drug, hormone, metal chelating group, radioactive metal complex, non-radioactive metal complex, echogenic agent, arylpolysulfonate, fused aryl, and radioisotope, and Bm is a bioactive domain selected from the group consisting of a bioactive peptide, protein, antibody, antibody fragment, oligosaccharide, drug, glycomimetic, cell, glycopeptide, peptidomimetic, hormone, metal chelating group, radioactive metal complex, non-radioactive metal complex, and echogenic agent; and $R_e$ is selected from the group consisting of hydrogen, a negatively-charged group, C1-C20 alkyl, C1-C14 aryl, C1-C20 alkoxyl, C1-C20 polyalkoxyalkyl, C1-C20 thioalkyl, C1-C20 carboxyl, C1-C20 aminoalkyl, C1-C20 hydroxyalkyl, C5-C20 polyhydroxyaryl, carbocyclic, heterocyclic, sulfonate, sulfate, thiol, sulfide, thioether, phosphonate, phosphate, phosphite, carboxylate, amino aryl, cyano, nitro, halogen, saccharide, peptide, protein, cell, glycopeptide, glycomimetic, peptidomimetic, antibody, antibody fragment, drug, hormone, metal chelating group, radioactive metal complex, non-radioactive metal complex, echogenic agent, arylpolysulfonate, fused aryl, and radioisotope;
$R^{205}$, $R^{206}$, $R^{207}$, $R^{208}$, $R^{209}$, $R^{210}$, $R^{211}$, $R^{212}$, and $R^{213}$ are independently selected from the group consisting of hydrogen, C1-C20 alkyl, C1-C14 aryl, C1-C20 alkoxyl, C1-C20 polyalkoxyalkyl, C1-C20 thioalkyl, C1-C20 carboxyl, C1-C20 aminoalkyl, C1-C20 hydroxyalkyl, C5-C20 polyhydroxyaryl, carbocyclic, heterocyclic, sulfonate, sulfate, thiol, sulfide, thioether, phosphonate, phosphate, phosphite, carboxylate, amino aryl, cyano, nitro, halogen, saccharide, peptide, protein, cell, glycopeptide, glycomimetic, peptidomimetic, antibody, antibody fragment, drug, hormone, metal chelating group, radioactive metal complex, non-radioactive metal complex, echogenic agent, arylpolysulfonate, fused aryl, and radioisotope,
$R^{214}$, $R^{215}$, and $R^{216}$ are independently selected from the group consisting of a hydrophilic linker, a lipophilic linker, and a bioactive domain (Bm), wherein $R^{214}$, $R^{215}$, and $R^{216}$ may combine to form a functional unit defined in the same manner as Bm, wherein Bm is a bioactive domain selected from the group consisting of a bioactive peptide, protein, antibody, antibody fragment, oligosaccharide, drug, glycomimetic, cell, glycopeptide, peptidomimetic, hormone, metal chelating group, radioactive metal complex, non-radioactive metal complex, and echogenic agent; and
$A_1$, $B_1$, and $D_1$ are independently selected from the group consisting of —O—, —S—, —Se—, —P—, —$PR_a$—$P(O)R_a$, —S(O)—, —$NR_a$, —$CR_aR_b$—, —C═O, C1-C10 alkyl, C1-C10 aryl, C1-C10 polyhydroxyalkyl, C1-C10 alkoxyl, —$CH_2(CH_2$—O—$CH_2)_c$—$CH_2$—O—, peptide, —$(CH_2)_d$—$CO_2H$, —$CH_2$—$(CH_2$—O—$CH_2)_e$—$CH_2$—CO—, —$(CH_2)_f$—$NR_b$—, and —$CH_2$—$(CH_2$—O—$CH_2)_g$—$CH_2NR_b$, provided $A_1$, $B_1$, and $D_1$ may together form a 5 to 20 membered carbocyclic or heterocyclic ring, optionally containing one or more oxygen, nitrogen, or sulfur atoms; wherein $R_a$ and $R_b$ are independently selected from the group consisting of hydrogen, C1-C20 alkyl, C1-C14 aryl, C1-C20 alkoxyl, C1-C20 polyalkoxyalkyl, C1-C20 thioalkyl, C1-C20 carboxyl, C1-C20 aminoalkyl, C1-C20 hydroxyalkyl, C5-C20 polyhydroxyaryl, carbocyclic, heterocyclic, sulfonate, sulfate, thiol, sulfide, thioether, phosphonate, phosphate, phosphite, carboxylate, amino aryl, cyano, nitro, halogen, saccharide, peptide, protein, cell, glycopeptide, glycomimetic, peptidomimetic, antibody, antibody fragment, drug, hormone, metal chelating group, radioactive metal complex, non-radioactive metal complex, echogenic agent, arylpolysulfonate, fused aryl, and radioisotope; and wherein the subscripts a, c, d, e, f, and g independently vary from 1 to 20.

2. The macrocyclic bioconjugate imaging agent of claim 1, wherein the imaging agent comprises Formula 29:

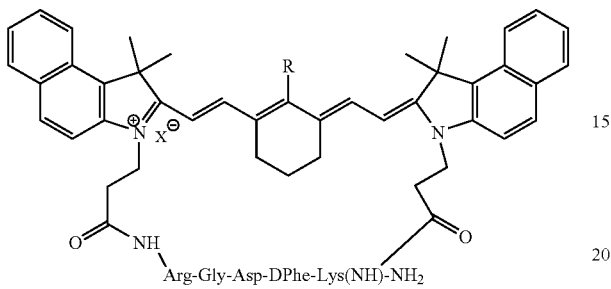

Formula 29 wherein:

R is selected from the group consisting of hydrogen, C1-C20 alkyl, C1-C14 aryl, C1-C20 alkoxyl, C1-C20 polyalkoxyalkyl, C1-C20 thioalkyl, C1-C20 carboxyl, C1-C20 aminoalkyl, C1-C20 hydroxyalkyl, C5-C20 polyhydroxyaryl, carbocyclic, heterocyclic, sulfonate, sulfate, thiol, sulfide, thioether, phosphonate, phosphate, phosphite, carboxylate, amino aryl, cyano, nitro, halogen, saccharide, peptide, protein, cell, glycopeptide, glycomimetic, peptidomimetic, antibody, antibody fragment, drug, hormone, metal chelating group, radioactive metal complex, non-radioactive metal complex, echogenic agent, arylpolysulfonate, fused aryl, and radioisotope; and X is an anion.

3. A composition comprising the bioconjugate macrocyclic imaging agent of either claim 1 or claim 2 further comprising a pharmaceutically acceptable carrier or excipient.

* * * * *

UNITED STATES PATENT AND TRADEMARK OFFICE
CERTIFICATE OF CORRECTION

Page 1 of 1

PATENT NO. : 7,850,946 B2
APPLICATION NO. : 10/559000
DATED : December 14, 2010
INVENTOR(S) : Samuel Achilefu et al.

It is certified that error appears in the above-identified patent and that said Letters Patent is hereby corrected as shown below:

Col. 53, line 46: "-$(CH_2)_a NR_b SO_3$-$(CH_2)$" should read

-- -$(CH_2)_a NR_b SO_3$-, $(CH_2)$ --

Signed and Sealed this
Eighth Day of November, 2011

David J. Kappos
*Director of the United States Patent and Trademark Office*

```
SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Gln(Trt)
<220> FEATURE:
<221> NAME/KEY: MOD_RES
<222> LOCATION: (2)
<223> OTHER INFORMATION: Trp(Boc)
<220> FEATURE:
<221> NAME/KEY: MOD_RES
<222> LOCATION: (6)
<223> OTHER INFORMATION: His(Trt)
<220> FEATURE:
<221> NAME/KEY: MOD_RES
<222> LOCATION: (9)
<223> OTHER INFORMATION: Lys(Boc)

<400> SEQUENCE: 1

Gln Trp Val Ala Gly His Leu Met Lys
  1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Trp Val Ala Gly His Leu Met Lys
  1               5
```